US012656227B2

(12) United States Patent
Ponomarev et al.

(10) Patent No.: US 12,656,227 B2
(45) Date of Patent: Jun. 16, 2026

(54) SENSING SYSTEM WITH IMPROVED FLUIDICS CONTROL

(71) Applicant: Analog Devices International Unlimited Company, Limerick (IE)

(72) Inventors: Youri Victorovitch Ponomarev, Rotselaar (BE); Erin Eda Evke, Boston, MA (US)

(73) Assignee: ANALOG DEVICES INTERNATIONAL UNLIMITED COMPANY, Limerick (IE)

( * ) Notice: Subject to any disclaimer, the term of this patent is extended or adjusted under 35 U.S.C. 154(b) by 666 days.

(21) Appl. No.: 18/055,779

(22) Filed: Nov. 15, 2022

(65) Prior Publication Data

US 2023/0152189 A1 May 18, 2023

Related U.S. Application Data

(60) Provisional application No. 63/280,496, filed on Nov. 17, 2021.

(51) Int. Cl.
| | |
|---|---|
| *G01N 1/20* | (2006.01) |
| *G01N 27/416* | (2006.01) |
| *G01N 33/50* | (2006.01) |

(52) U.S. Cl.
CPC ....... *G01N 1/2035* (2013.01); *G01N 27/4163* (2013.01); *G01N 33/5008* (2013.01); *G01N 2001/205* (2013.01)

(58) Field of Classification Search
CPC .......... G01N 1/2035; G01N 2001/205; G01N 27/4162–4168; G01N 33/49;

(Continued)

(56) References Cited

U.S. PATENT DOCUMENTS

| | | | |
|---|---|---|---|
| 4,797,191 A | 1/1989 | Metzner | |
| 4,995,959 A | 2/1991 | Metzner | |

(Continued)

FOREIGN PATENT DOCUMENTS

| | | |
|---|---|---|
| CN | 106716137 A | 5/2017 |
| CN | 118251175 A | 6/2024 |

(Continued)

OTHER PUBLICATIONS

International Search Report and Written Opinion in PCT/EP2022/082114, dated Feb. 7, 2023.

(Continued)

*Primary Examiner* — James Lin
*Assistant Examiner* — Vivian A Tran
(74) *Attorney, Agent, or Firm* — Knobbe, Martens, Olson & Bear, LLP

(57) ABSTRACT

Methods and apparatuses for fluid sensing system are disclosed. The method can include providing a first portion of a sample fluid in a sensing channel, holding the first portion of the sample fluid in the sensing channel for a first diffusion period, after the first diffusion period, providing a second portion of the sample fluid in the sensing channel, holding the second portion of the sample fluid in the sensing channel for a second diffusion period, and after the second diffusion period, sensing the second portion of the sample fluid in the sensing channel by a sensing element. Providing pulses of sample with intervening diffusion periods can produce more uniform analyte concentration across sensors with less overall volume of sample fluid.

14 Claims, 24 Drawing Sheets

(58) Field of Classification Search
CPC ....... G01N 33/492–4925; G01N 33/50; G01N
33/5008
See application file for complete search history.

(56) References Cited

U.S. PATENT DOCUMENTS

| | | | |
|---|---|---|---|
| 9,239,322 B2 | 1/2016 | Mahoney et al. | |
| 10,830,692 B2 | 11/2020 | Wang et al. | |
| 12,196,705 B2 | 1/2025 | Bolognia et al. | |
| 2004/0163970 A1 | 8/2004 | Sin et al. | |
| 2009/0156922 A1 | 6/2009 | Goldberger et al. | |
| 2010/0168546 A1 | 7/2010 | Kamath et al. | |
| 2011/0077480 A1 | 3/2011 | Bloom et al. | |
| 2013/0199998 A1 | 8/2013 | Kelly | |
| 2018/0372719 A1* | 12/2018 | Frischauf | G01N 33/492 |
| 2020/0030515 A1 | 1/2020 | Merchant | |
| 2020/0182891 A1 | 6/2020 | Di Tullio et al. | |
| 2022/0291165 A1 | 9/2022 | Bolognia et al. | |
| 2023/0149608 A1 | 5/2023 | Ponomarev et al. | |
| 2024/0035933 A1 | 2/2024 | Bolognia et al. | |

FOREIGN PATENT DOCUMENTS

| | | | |
|---|---|---|---|
| EP | 0226593 B1 | | 1/1992 |
| EP | 4432920 | | 9/2024 |
| JP | S59-6064 | | 1/1984 |
| JP | S59-6065 | | 1/1984 |
| JP | H02-57961 | | 2/1990 |
| JP | H0257961 A | * | 2/1990 |
| JP | H04-84750 | | 3/1992 |
| JP | 2003-262613 | | 9/2003 |
| JP | 2006130306 A | | 5/2006 |
| JP | 7669593 | | 4/2015 |
| JP | 2018038843 A | | 3/2018 |
| TW | I 870954 | | 1/2025 |
| WO | WO 2020/176663 A1 | | 9/2020 |
| WO | WO 2023/088954 A1 | | 5/2023 |

OTHER PUBLICATIONS

International Preliminary Report on Patentability in PCT/EP2022/082114, dated May 2, 2024 in 6 pages.

* cited by examiner

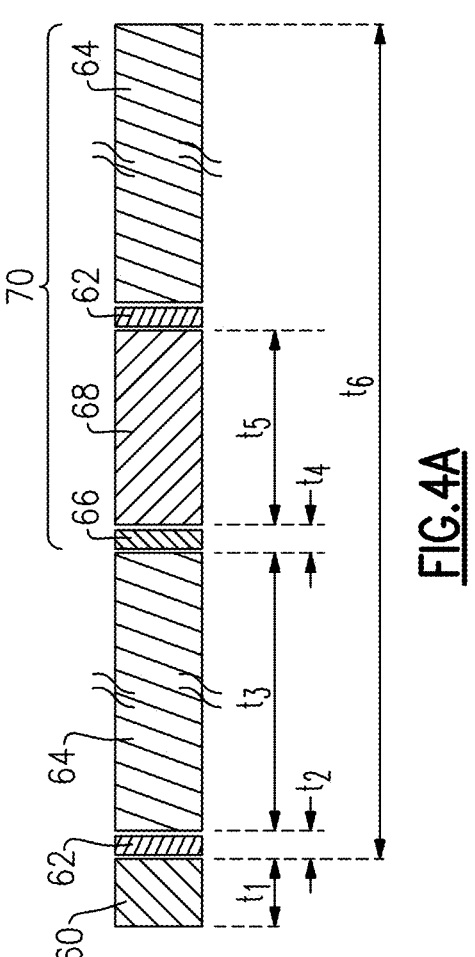

FIG.4A

| | DESCRIPTION | PARAMETER | EXAMPLE TIMING |
|---|---|---|---|
| | TRANSDUCER CHIP DRY, STARTING STATE. APPLICATION FLUID CIRCUIT IS IN BYPASS MODE. | $t_1$ | 30 SEC |
| | FLUSH TRANSDUCER WITH CALIBRATION FLUID, FULL EXCHANGE OF FLUID VOLUME IN TRANSDUCER AREA. EXCESS LIQUID DIRECTED TO WASTE COMPARTMENT. | $t_2$ | 1 SEC |
| | STEADY STATE ACROSS TRANSDUCER, IN CALIBRATION FLUID, WAITING FOR MEASUREMENT REQUEST. APPLICATION FLUID CIRCUIT IS IN BYPASS MODE. | $t_3$ | 1 ... 120 MIN |
| | ON MEASUREMENT REQUEST: FLUSH TRANSDUCER WITH ANALYTE, FULL EXCHANGE OF FLUID VOLUME IN TRANSDUCER AREA. EXCESS LIQUID DIRECTED TO WASTE COMPARTMENT. | $t_4$ | 1 SEC |
| | STEADY STATE ACROSS TRANSDUCER, IN ANALYTE. SENSOR MEASUREMENTS PERFORMED. APPLICATION FLUID CIRCUIT IS IN BYPASS MODE. | $t_5$ | 30 SEC |
| | TOTAL OPERATIONAL LIFE OF CARTRIDGE | $t_6$ | 72 HRS |

FIG.4B

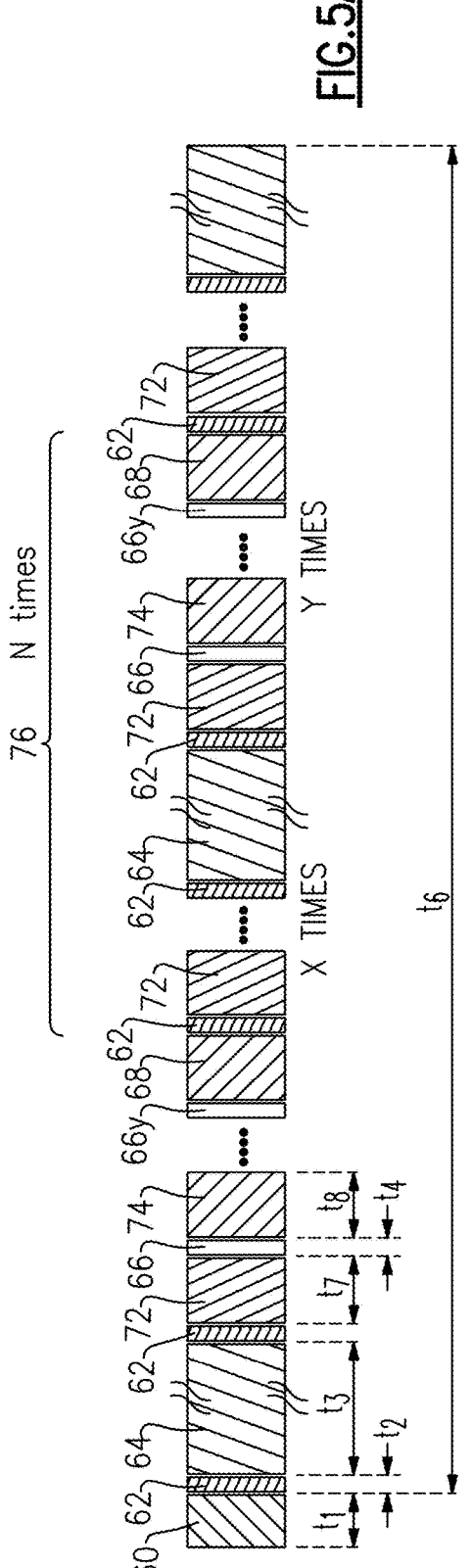

FIG.5A

| | DESCRIPTION | PARAMETER | EXAMPLE TIMING |
|---|---|---|---|
| | TRANSDUCER CHIP DRY, STARTING STATE. | $t_1$ | 30 SEC |
| | FLUSH TRANSDUCER WITH CALIBRATION FLUID, FULL EXCHANGE OF FLUID VOLUME IN TRANSDUCER AREA | $t_2$ | 1 SEC |
| | STEADY STATE ACROSS TRANSDUCER, IN CALIBRATION FLUID | $t_7$ | 10 SEC |
| | STEADY STATE ACROSS TRANSDUCER, IN CALIBRATION FLUID, WAITING FOR MEASUREMENT REQUEST | $t_3$ | 1 ... 90 MIN |
| | FLUSH TRANSDUCER WITH ANALYTE, FULL EXCHANGE OF FLUID VOLUME IN TRANSDUCER AREA | $t_4$ | 1 SEC |
| | STEADY STATE ACROSS TRANSDUCER, IN ANALYTE. | $t_8$ | 10 SEC |
| | TOTAL OPERATIONAL LIFE OF CARTRIDGE | $t_6$ | 72 HRS |

FIG.5B

TIME=145s

TIME=90s

TIME=45s

TIME=20s

TIME=1s

VELOCITY MAGNITUDE (m/s), BOUNDARY PROBE 1

SURFACE: CONCENTRATION (mol/m³) STREAMLINE: TOTAL FLUX

TIME=3s, flow_rate_1exch_p_s=0.00128 m/s

SURFACE: CONCENTRATION (mol/m³) STREAMLINE: TOTAL FLUX

TIME=2.5s, flow_rate_1exch_p_s=0 m/s

SURFACE: CONCENTRATION (mol/m ) STREAMLINE: TOTAL FLUX

TIME=3s, flow_rate_1exch_p_s=0.00128 m/s

SURFACE: CONCENTRATION (mol/m ) STREAMLINE: TOTAL FLUX

TIME=5s, flow_rate_1exch_p_s=0 m/s

SENSING SYSTEM WITH IMPROVED FLUIDICS CONTROL

RELATED APPLICATIONS

This application claims the benefit of U.S. Provisional Application No. 63/280,496, entitled "SENSING SYSTEM WITH IMPROVED FLUIDICS CONTROL," filed Nov. 17, 2021, the entire disclosure of which is incorporated herein by reference for all purposes.

This application also relates to U.S. application Ser. No. 17/654,177 (US Publication No. 2022/0291165), filed Mar. 9, 2022, the entire disclosure of which is incorporated herein by reference for all purposes.

BACKGROUND

Field

The field relates to methods of controlling a fluid sensor system, and systems with fluidic control.

Description of the Related Art

Many medical treatment procedures are performed in a hospital or outpatient facility, such that the patient must typically be admitted to the facility to undergo treatment. Treatment procedures, such as kidney dialysis procedures, are often performed on a regular basis, which can be inconvenient, time-consuming, and economically costly to the patient and the clinician. Enabling such treatment procedures to be performed in one location (e.g., the patient's home) can advantageously improve the convenience, efficiency, and affordability of the procedures.

SUMMARY

For purposes of summarizing the disclosure, certain aspects, advantages, and novel features of the innovations have been described herein. It is to be understood that not necessarily all such advantages can be achieved in accordance with any particular embodiment. Thus, the innovations described herein can be embodied or carried out in a manner that achieves or optimizes one advantage or group of advantages as taught herein without necessarily achieving other advantages as can be taught or suggested herein.

In one aspect, a method of operating a fluid sensing system is disclosed. The method can include providing a first portion of a sample fluid in a sensing channel, holding the first portion of the sample fluid in the sensing channel for a first diffusion period, after the first diffusion period, providing a second portion of the sample fluid in the sensing channel, holding the second portion of the sample fluid in the sensing channel for a second diffusion period, and after the second diffusion period, sensing the second portion of the sample fluid in the sensing channel by a sensing element.

In one embodiment, the method further includes calibrating the sensing element in the sensing channel using a calibration fluid. The calibration fluid can be provided in the sensing channel in multiple pulses. Calibrating the sensing element can further include holding at least a portion of the calibration fluid for diffusion to occur. Calibrating the sensing element can include providing the calibration fluid into 2-6 portions and providing the portions in sequence with diffusion periods therebetween.

In one embodiment, the method further includes providing a third portion of the sample fluid in the sensing channel after the first diffusion period and before providing the second portion of the sample fluid, and holding the third portion of the sample fluid in the sensing channel for a third diffusion period. The method can further include providing a fourth portion of the sample fluid in the sensing channel after the third diffusion period and before providing the second portion of the sample fluid, and holding the fourth portion of the sample fluid in the sensing channel for a fourth diffusion period.

In one embodiment, each subsequent portion of the sample fluid directly replaces the prior portion after the prior portion's diffusion period.

In one embodiment, the sensing element includes an optical sensing element or an electrochemical sensing element.

In one embodiment, the method further includes providing an air segment prior to providing the first portion of the sample fluid.

In one embodiment, the first diffusion period is in a range between 5 seconds and 20 seconds.

In one embodiment, a volume of the first portion is between 25% and 200% of a volume of the sensing channel.

In one embodiment, the sensing element includes three to fifteen electrodes. A first electrode of the sensing element can detect a first constituent in the second portion of the sample fluid and a second electrode of the sensing element can detect a second constituent in the second portion of the sample fluid different from the first constituent.

In one aspect, a method of operating a fluid sensing system is disclosed. The method can include flushing at least a portion of a first fluid in a sensing channel with a second fluid, holding the second fluid in the sensing channel for a diffusion period, after the diffusion period, flushing at least a portion of the second fluid in the sensing channel with a third fluid, and sensing the third fluid in the sensing channel by a sensing element. The first fluid and the second fluid are different fluids. The second fluid and the third fluid are from the same fluid sample or calibration fluid.

In one embodiment, the diffusion period is in a range between 5 seconds and 20 seconds.

In one embodiment, the method further includes flushing the third fluid by a fourth fluid, and holding the fourth fluid in the sensing channel for a second diffusion period.

In one embodiment, an apparatus includes a control module for conducting the methods. The control module can be electrically and mechanically coupled to a sensor module that comprises the sensing channel and the sending element.

In one aspect, a sensing system is disclosed. The sensing system can include a sensing module having a sensing element positioned between an inlet valve and an outlet valve, and a reader including a controller. The controller is configured to open the inlet and outlet valves to provide a first portion of a sample fluid in a sensing channel, close the inlet and outlet valves to hold the first portion of the sample fluid in the sensing channel for a first diffusion period, after the first diffusion period, open the inlet and outlet valves to provide a second portion of the sample fluid in the sensing channel, close the inlet and outlet valves to hold the second portion of the sample fluid in the sensing channel for a second diffusion period, and after the second diffusion period, operate a sensing element to sense the second portion of the sample fluid in the sensing channel.

In one embodiment, the sensing element includes a plurality of electrodes.

In one embodiment, the sensing element is configured to send a signal indicative of respective constituent components of the second portion of the sample fluid.

BRIEF DESCRIPTION OF THE DRAWINGS

Specific implementations will now be described with reference to the following drawings, which are provided by way of example, and not limitation.

FIG. 4A is a timing diagram of operating a sensor module of a sensor system.

FIG. 4B is a chart showing example timings of various states in the operation of the sensor module of FIG. 4A.

FIG. 5A is a timing diagram of operating a sensor module of a sensor system according to an embodiment.

FIG. 5B is a chart showing example timings of various states in the operation of the sensor module of FIG. 5A.

DESCRIPTION

In a medical treatment procedure, it is desirable to monitor content(s) of a fluid, such as the electrolyte content of dialysate or blood. Biological fluid content sensors can include sensor devices or chips that operate on optical or electrochemical sensing principles. In either case, it is desirable to calibrate the sensors between samples of the fluid.

When replacing a first fluid (e.g., a calibration fluid or an analyte) in a sensing channel of a sensor module with a second fluid (e.g., an analyte or a calibration fluid), a relatively large amount of the second fluid may need to be provided to sufficiently measure the second fluid because a residue of the first fluid may remain in the channel. However, it can be undesirable to use the relatively large amount of the second fluid to effectively (e.g., completely) displace the first fluid. For example, when there is only a limited amount of the second fluid, it can be important to replace the first fluid with the second fluid efficiently. In some embodiments, one of the fluids can be an inert fluid (e.g., air or distilled water). Advantageously, however, embodiments described herein can replace one active fluid with another active fluid (e.g., analyte with calibration fluid or vice versa), thereby avoiding the time and volume of fluid needed to provide an inactive fluid (e.g., air or distilled water) between the analyte and calibration fluids.

Various embodiments disclosed herein relate to a fluid sensor module configured to connect in-line with a treatment system. The treatment system can comprise a medical device, such as a dialysis treatment system. Various embodiments disclosed herein relate to fluid sensing systems that can efficiently replace the first fluid in a sensing channel with the second fluid in the sensing channel. In some embodiments, a total amount of second fluid can be divided into a plurality of portions, and each portion can be provided into the channel separately in sequence. This process of separately providing portions of the second fluid can flush or directly replace a previously existing fluid in the sensing channel (e.g., the first fluid or a portion of the second fluid). At each flush, the flow is paused to allow the second fluid to stay in the sensing chamber for diffusion to occur to equilibrate the concentration in the active fluidics portion of the sensing element. Each portion can have a volume that is equal to or about a volume of the sensing channel. For example, the volume of the sensing channel can be between 25 μL to 100 μL in an example employing 12 different sensors along the channel (i.e., about 2 μL to 8 μL on average for each sensor).

Figure 1:
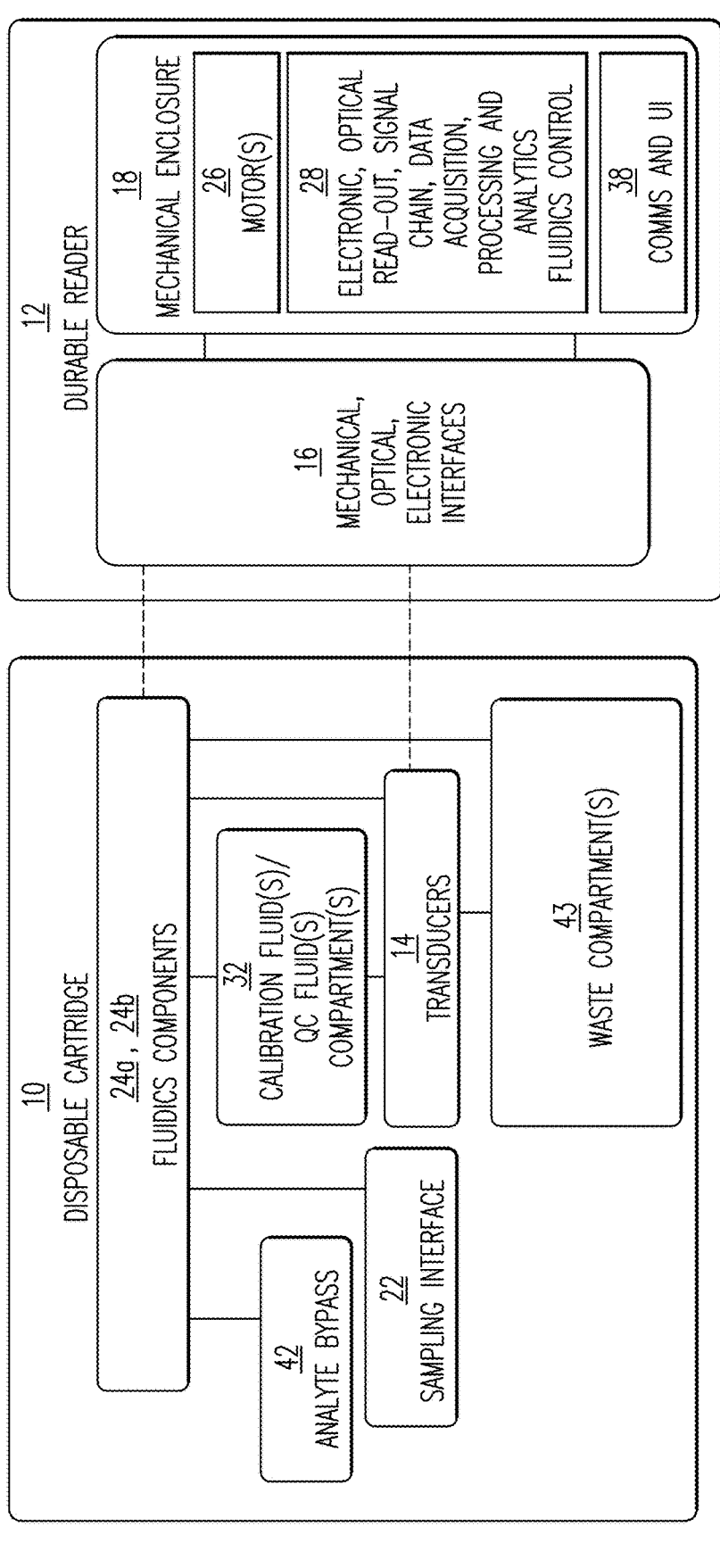
FIG. 1 is a block diagram of a fluid sensing system 1.
Figure 2:
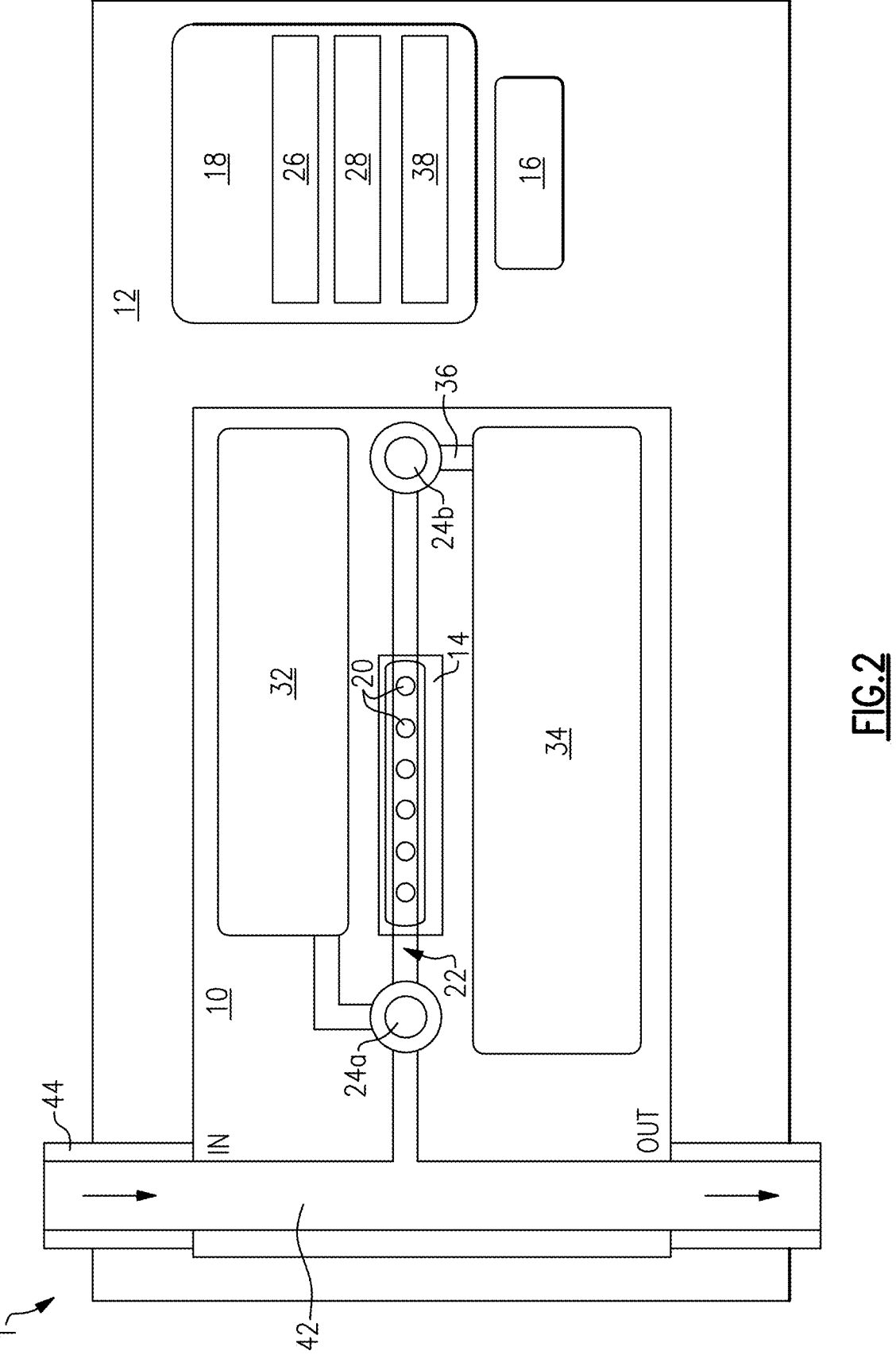
FIG. 2 is a system outline of the fluid sensing system of FIG. 1.

FIG. 1 shows a block diagram of a fluid sensing system 1 according to an embodiment. FIG. 2 is a system outline of the fluid sensing system 1 according to an embodiment. The fluid sensing system 1 can include a sensor module 10 and a reader 12. The sensor module 10 can be disposable. The sensor module 10 can also be referred to as a sensor cartridge. In some embodiments, the sensor module 10 can be removably coupled to the reader 12. The sensor module 10 can include one or more optical sensor(s) or electro-chemical sensor(s), or a combination of optical and electro-chemical sensors. For example, the sensor module 10 can include a sensing assembly that includes a sensing element 14. The sensor system 1 can include an interface unit 16. The interface unit 16 can function as an interface between the sensor module 10 and the reader 12, and be part of the sensor module 10 and/or the reader 12 (shown as part of the reader 12 in FIG. 1). The reader 12 can include a controller 18. In some embodiments, the reader 12 and the sensor module 10 can communicate through the interface unit 16.

Figure 3:
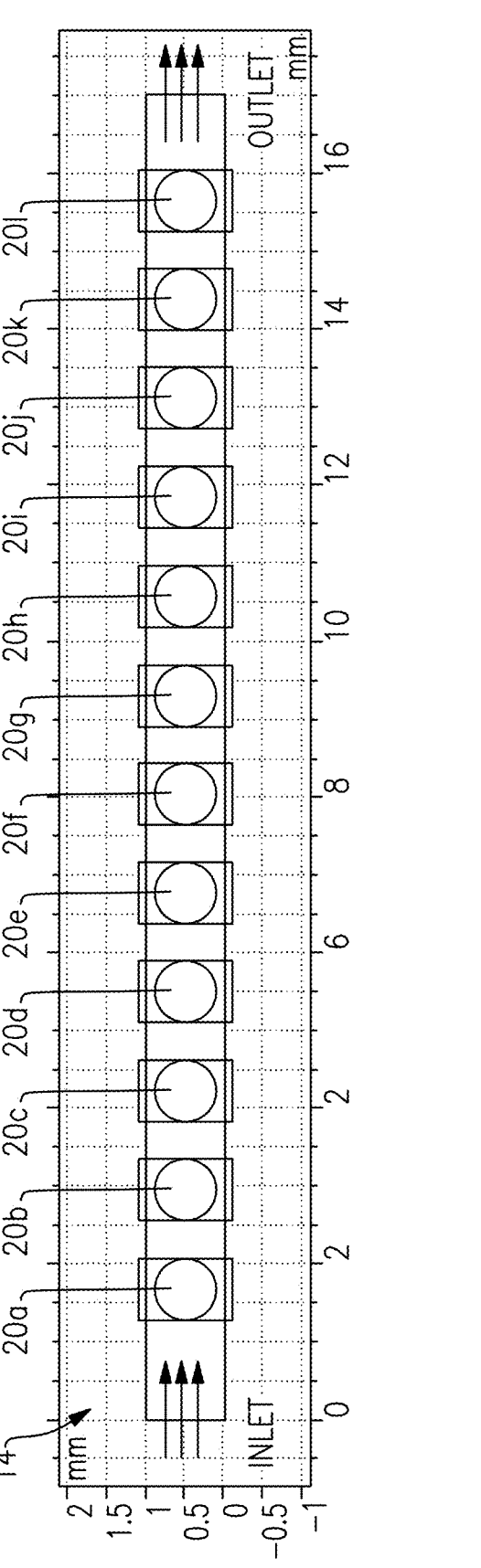
FIG. 3 is a schematic top plan view of a sensing element.

The sensing element 14 can include a plurality of functionalized electrodes 20 (e.g., twelve electrodes as shown in FIG. 3) that, when exposed to the sample fluid, transmit a signal indicative of particular constituent component(s) of the sample fluid. In some embodiments, the sensing element 14 can include any suitable number of transducers or electrodes 20 (FIG. 2). For example, the sensing element 14 can include more than two, more than three, more than five, more than ten, or even greater number of transducers or electrodes 20. For example, the sensing element 14 can include three to fifteen electrodes, six to fifteen electrodes, or ten to fifteen electrodes. In some embodiments, all or some of the electrodes 20 can be configured (along with the electronics of the reader 12) to sense the same constituent. In some other embodiments, each electrode 20 can be configured (along with the electronics of the reader 12 to sense a different constituent. Examples of the sensors could be ion sensors (both anions and cations such as Na+, K+, Ca++, pH, Mag++, Cl−, NH3−), metabolite sensors (e.g., Creatinine, Glucose, Urea), dissolved gasses sensors (e.g., pO2, pCO2), biomarker sensors (e.g., IL-6, MMP, and in general cytokines) and also configure to function as reference potential and counter electrodes (to enable accurate potentiometric and amperometric sensors measurements). The sensing element 14 can be positioned in a sensing channel 22 that is configured to receive calibration fluid and/or the sample fluid. An inlet valve 24a can be positioned at an upstream end of the sensing channel 22 and an outlet valve 24b can be positioned at a downstream end of the sensing channel 22.

During operation of the fluid sensing system 1, the inlet valve 24a and the outlet valve 24b can be controlled to let fluids enter and exit the sensing channel 22. In some embodiments, a valve motor 26 disposed in the reader 12 can connect to the valves 24a, 24b by way of a valve connector (e.g., a valve opening) configured to operably connect to a motor shaft of the valve motor 26. Processing electronics 28 in the reader 12 can be configured to send instructions to the valve motor 26 to open/close the inlet valve 24a and the outlet valve 24b. In some embodiments, the outlet valve 24b can be positioned between the sensing element 14 and a waste compartment 34. The outlet valve 24b can separate the sensing channel 22 and a waste channel 36. In some embodiments, the user (e.g., patient or clinician) can manually operate the inlet and outlet valves 24a, 24b by engaging a user interface (UI) 38 of the reader 12. The UI 38 of the reader 12 can comprise a touch screen and/or buttons that enable the user and/or clinician to interact with the reader 12. In some embodiments, the UI 38 can include a display that indicates the levels of the constituent components in the fluids.

A fluid pathway 42 of the sensor module 10 can be coupled to a tubing set 44 of a treatment system, such as a dialysis treatment system. For example, the fluid pathway 42 can connect in-line with the tubing set 44 of the treatment system. The inlet valve 24a can separate the sensing channel 22 and the fluid pathway 42. In some embodiments, the inlet valve 24a can be a multi-way (e.g., three-way) valve that has a closed state that blocks a fluid to enter the sensing channel 22, a first open state that provides fluid communication between the sensing channel 22 and a calibration reservoir 32 that stores a calibration fluid, and a second open state that provides fluid communication between the sensing channel 22 and the fluid pathway 42.

FIG. 3 is a schematic top plan view of a sensing element 14. In the illustrated embodiment, the sensing element 14 includes first to twelfth electrodes 20a-20l. As described herein, the sensing element 14 can include any suitable number of transducers or electrodes. The sample fluid can interact with the first to twelfth electrodes 20a-20l and, in response, the sensor module 10 can transmit a signal to the reader 12 indicative of respective constituent components of the sample fluid. In some embodiments, all or some of the electrodes 20a-20l can be configured (along with the electronics of the reader 12) to sense the same constituent. In some other embodiments, each electrode 20a-20l can be configured (along with the electronics of the reader 12) to sense a different constituent.

In the illustrated embodiment, a length of the sensing element 14 can be about 17 mm. The length of the sensing element 14 can depend at least in part on the number of electrodes included in the sensing element 14. In some embodiments, the length of the sensing element 14 can be in a range between 10 mm and 30 mm, 15 mm and 30 mm, 10 mm and 25 mm, or 15 mm and 20 mm. For example, each electrode can have a diameter of about 0.75 mm, and a spacing between an electrode to an adjacent electrode of about 0.5 mm. Various measurement results disclosed herein are derived using the sensing element 14 of FIG. 3. However, any suitable sensing element for measuring respective constituent components of the sample fluid can be implemented in the sensor modules disclosed herein.

FIG. 4A shows a timing diagram of operating a sensor module of a sensor system. FIG. 4B is a chart showing example timings of various states in the operation of the sensor module. In some embodiments, the operation of the sensor module (e.g., the sensor module 10) can be controlled at least in part by the reader 12. In a first state (a starting state 60), the sensing element or the electrodes of the sensing element 14 can be dry and free from a liquid. In the starting state 60, the sensor module 10 can be in a bypass mode in which the sample fluid does not enter the sensor channel 22. A duration t1 of the starting state 60 can be about 30 seconds.

A second state (a calibration flush state 62) can follow the starting state 60. In the calibration flush state 62, the electrodes of the sensing element 14 can be flushed with a calibration fluid through the sensing channel 22. A duration t2 of the calibration flush state 62 can be about 1 second. The calibration liquid can comprise, for example, water with known concentrations of species (e.g., sodium, potassium, pH, calcium, etc.) to calibrate the sensing element 14.

A third state (a stand-by state 64) can follow the calibration flush state 62. In the stand-by state 64, the calibration fluid can stay in the sensing channel 22 until a measurement request is received. In the stand-by state 64, the sensor module 10 can be in the bypass mode. A duration t3 of the stand-by state 64 can be about 1 minute to 120 minutes.

A fourth state (a sample flush state 66) can follow the stand-by state 64. In the sample flush state 66, the sample fluid or analyte can be provided. The sensor module 10 can be in a sample flush mode in which the inlet valve 24a and the outlet valve 24b are opened to allow the sample fluid to flow in the sensing channel 22. The inlet valve 24a can be a three-way valve that has a closed state that blocks a fluid to enter the sensing channel 22, a first open state that provides fluid communication between the sensing channel 22 and the calibration reservoir 32, and a second open state that provides fluid communication between the sensing channel 22 and the fluid pathway 42. For example, the calibration fluid in the sensing channel 22 can be flushed and replaced with the sample fluid. In some embodiments, an excess fluid can be directed to the waste compartment 34. A duration t4 of the sample flush state 66 can be about 1 second.

A fifth state (a measurement state 68) can follow the sample flush state 66. In the measurement state 68, the sample fluid can stay in the sensing channel 22 and interact with the electrodes of the transducer chip 14 for measurement. In the measurement state 68, the sensor module 10 can be in the bypass mode in which the inlet valve 24a and the outlet valve 24b are closed. A duration t5 of the fifth state 68 can be about 30 seconds.

After the measurement state 68, a cleaning process (the calibration flush and stand-by states 62, 64) can follow to clean the sensing channel 22 and surfaces of the electrodes 20 of the sensing element 14. After cleaning the sensing channel 22 and the surfaces of the electrodes 20, another measurement can take place upon request and repeat the measurement process (the sample flush and measurement states 66, 68). The cleaning and measurement cycle 70 can repeat a number of times. The total number of times (N times) of the cleaning and measurement cycle 70 can be determined based at least in part on a size of the calibration reservoir 32 and/or a size of the waste compartment 34. A total operation life t6 can be about 72 hours.

In the operation described with respect to FIGS. 4A and 4B, the sample fluid is provided in one single dose. Similarly, the calibration fluid is provided in one single dose, as well. In order to achieve a sufficiently high concentration of the sample fluid, or to sufficiently clean the electrodes 20 by the calibration fluid with such single dose processes, significant amount of the sample fluid or the calibration fluid may be needed. Also, when there is a limited amount of the sample fluid is available, a sufficiently high concentration of the sample fluid in the sensing channel 22 may not be obtained and accuracy of the measurement may not be ideal. Also, the total number of measurements that can be performed by the sensor module 10 over its life may depend on the total amount of the calibration fluid. Therefore, using more calibration fluid in each cleaning process can reduce the total number of measurements that can be performed by the sensor module 10.

In FIGS. 5A and 5B, improved operations of the sensor module 10 that overcome the shortcomings of the operation of FIGS. 4A and 4B are described. FIG. 5A shows a timing diagram of operating a sensor module of a sensor system according to an embodiment. FIG. 5B is a chart showing example timings of various states in the operation of the sensor module. In a first state (starting state 60), the channel can be dry. In some applications, a duration t1 of the starting state 60 can be about 30 seconds. For example, the duration t1 of the starting state 60 can be between 5 seconds and 10 minutes, 10 seconds and 5 minutes, or 20 seconds and 1 minute.

In a second (calibration flush) state 62, the inlet valve 24a and the outlet valve 24b can be opened to flush a first portion of calibration fluid into the sensing channel 22. The calibration liquid or fluid (also referred to as a quality control fluid, or QC fluid, e.g., a biocompatible fluid such as water, saline, etc.) can be provided in a calibration reservoir 32 of the sensor module 10. In some embodiments, there may be a plurality of calibration reservoirs including the calibration reservoir 32. The plurality of calibration reservoirs may store different calibration fluids. For example, each reservoir of the plurality of calibration reservoirs can be configured to each store a different calibration fluid with known quantities of one or more constituents to be sensed that is suitable for a particular sensor (such as ion sensors, metabolite sensors, dissolved gasses sensors, or biomarker sensors) implemented by the sensing element 14. The calibration liquid or fluid can comprise, for example, water with known concentrations of species (e.g., sodium, potassium, pH, calcium, etc.) to calibrate the sensors. In some embodiments, the calibration fluid can serve to reset the sensor module 10 by flushing the sensing element 14 of older sample fluid and/or other debris. Thus, the calibration fluid may also be deemed a purge fluid. The processing electronics 28 can be configured to recognize that the sample fluid is in fluid communication with each of the bare or functionalized electrodes 20. In some applications, a duration t2 of the second state 62 can be about 1 second. For example, the duration t2 of the second state 62 can be between 0.5 seconds and 5 seconds, between 0.5 seconds and 3 seconds, or between 0.75 seconds and 3 seconds.

In a third (calibration diffusion) state 72, the inlet valve 24a and the outlet valve 24b can be closed, and the calibration fluid can stay in the sensing channel 22. In some embodiments, the calibration flush state 62 and the calibration diffusion state 72 can be repeated. When the calibration flush state 62 and the calibration diffusion state 72 are repeated, it does not necessarily repeat the exact same processes. For example, an amount of the sample fluid in and/or a duration of the calibration flush state 62 and/or the calibration diffusion state 72 may vary in a series of a repeated process. For example, a total amount of the calibration fluid for one calibration process can be divided into x portions comprising a first portion to an $x^{th}$ portion, and the second state and the third state can be conducted in a first cycle (or subcycle) x times in sequence. In some embodiments, x can be between 2 and 10. In some embodiments, x can be between 3 and 6. In some applications, a duration t7 of the calibration diffusion state 72 can be about 10 seconds. For example, the duration t7 of the calibration diffusion state 72 can be between 5 seconds and 20 seconds, or between 5 seconds and 15 seconds. In some embodiments, multiple calibration flush states 62 can occur without an intervening the calibration diffusion state 72. In some embodiments, a volume of a portion of the x portions of the calibration fluid can be 25% to 200%, 50% to 150%, or 75% to 125% of a volume of the sensing channel 22. In some embodiments, a volume of a portion of the x portions of the calibration fluid can be about the volume of the sensing channel 22, about twice the volume of the sensing channel, 22 about three times the volume of the sensing channel.

In a fourth (stand-by) state 64, measurement of the calibration fluid can take place for calibration. The calibration can ensure proper functioning of the sensing element 14. In some embodiments, the sensing element 14 can include an optical-to-electronic signal transducer. The inlet valve 24a and the outlet valve 24b can remain closed and the calibration fluid can stay in the sensing channel 22 until a measurement of a sample fluid (an analyte) is initiated. The second state to the fourth state can constitute a calibration process. In some applications, a duration t3 of the stand-by state 64 can be about 1 minute to 90 minutes. For example, the duration t3 of the stand-by state 64 can be between 1 minute and 60 minutes, between 30 minutes and 90 minutes, or between 10 minutes and 60 minutes.

In a fifth (sample flush) state 66, the inlet valve 24a and the outlet valve 24b can be opened to flush a first portion of the sample fluid into the sensing channel 22. In some embodiments, a portion of the calibration fluid can be directed to the waste compartment 34 through the waste channel 36. In some applications, a duration t4 of the sample flush state 66 can be about 1 second. For example, the duration t4 of the sample flush state 66 can be between 0.5 seconds and 5 seconds, between 0.5 seconds and 3 seconds, or between 0.75 seconds and 3 seconds.

In a sixth (sample diffusion) state 74, the inlet valve 24a and the outlet valve 24b can be closed for a period of time (e.g., a first diffusion period) that allows for diffusion to occur to equilibrate the concentration in the active fluidics portion of the sensing element 14. In some embodiments, the sample flush state 66 and the sample diffusion state 74 can be repeated, with a second portion replacing the first portion and a subsequent diffusion period (e.g., a second diffusion period) to equilibrate the concentration in the active fluidics portion of the sensing element 14. When the sample flush state 66 and the sample diffusion state 74 are repeated, it does not necessarily repeat the exact same processes. For example, an amount of the sample fluid in and/or a duration of the sample flush state 66 and/or the sample diffusion state 74 may vary in a series of a repeated process. For example, a total amount of the sample fluid for a particular measurement can be divided into y portions comprising a first portion to a y$^{th}$ portion, and the sample flush state 66 and the sample diffusion state 74 can be conducted in a second cycle (or subcycle) y times in sequence. In some embodiments, y can be between 2 and 10. In some embodiments, y can be between 3 and 6. In some applications, a duration t8 of the sample diffusion state 74 can be about 10 seconds. For example, the duration t8 of the sample diffusion state 74 can be between 5 seconds and 20 seconds, or between 5 seconds and 15 seconds. In some embodiments, multiple sample flush states 66 can occur without an intervening sample diffusion state 74. In some embodiments, a volume of a portion of the y portions of the sample fluid can be 25% to 200%, 50% to 150%, or 75% to 125% of a volume of the sensing channel 22.

In a seventh (last sample flush) state 66y, the inlet valve 24a and the outlet valve 24b can be opened to flush the y$^{th}$ portion of the sample fluid into the sensing channel 22. As the number of times a portion of the sample fluid is flushed increases, a concentration of the sample fluid in the sensing channel 22 can increase. For example, after the y$^{th}$ flush, the concentration of the sample fluid can be more than 80%, more than 85%, more than 90%, more than 95%, or more than 97.5%.

In an eighth (measurement) state 68, the inlet valve 24a and the outlet valve 24b can be closed for a period of time as in the sample diffusion state 74, and measurement of the sample fluid can take place. The sensor module 10 can transmit a signal indicative of a particular constituent component of the sample fluid to the reader 12. The processing electronics 28 of the reader 12 can control the operation of sensor module 10.

The above operation (a cycle or supercycle) 76 that includes the calibration flush state 62, the calibration diffusion state 72, the stand-by state 64, the sample flush state 66, sample diffusion state 74, the last sample flush state 66y and the measurement state 68) can be repeated N times for different sample fluids. The total number of times (N times) can depend at least in part on, for example, a size of a calibration reservoir 32 and/or a size of the waste compartment 34. N will depend at least in part on application requirements and can range from 10 to 2000. In one example, a sensing system for inclusion in a dialysis system can be configured for N=95 samples over about 3 days. Therefore, a total operational life t6 over N samples of the sample module 10 can be about 72 hours. For example, the total operational life t6 over N samples of the sample module 10 can be in a range between 24 hours and 240 hours, 36 hours and 168 hours, 48 hours and 144 hours.

As described above, both the calibration flush state 62 and the calibration diffusion state 72 (a calibration process), and the sample flush state 66 and the sample diffusion state 74 (a measurement process), can be repeated in first and second subcycles, respectively. However, in some embodiments, only the calibration flush state 62 and the calibration diffusion state 72 (the calibration process) can be repeated, or only the sample flush state 66 and the sample diffusion state 74 (the measurement process) can be repeated.

Figures 6A, 6B, 6C, 6D, 6E, 6F:
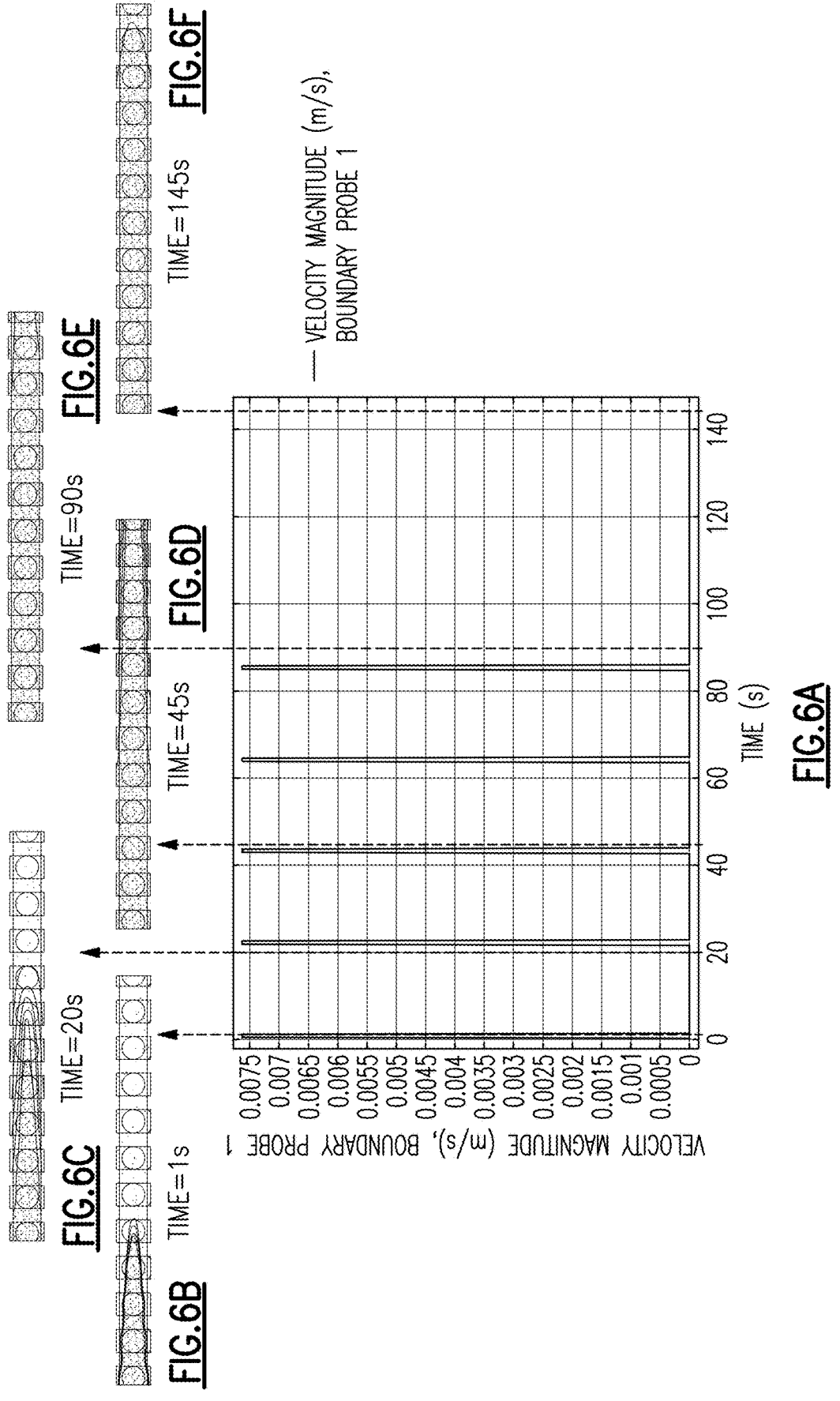
FIG. 6A is a graph showing timings of five pulses (flushes) of a particular fluid to replace an existing fluid in a simulation.
FIGS. 6B-6F show concentration distributions of the sample fluid over a sensing element at various time periods.

FIG. 6A is a graph showing timings of five pulses (flushes) of a particular fluid (e.g., the sample fluid) to replace an existing fluid (e.g., the calibration fluid) in a simulation. Referring to FIG. 5A, in FIG. 6A the sample fluid is divided into y=5 portions comprising a first portion to a 5$^{th}$ portion, and the process comprises four sample flush states 66 each followed by a sample diffusion state 74, and the last sample flush state 66y. FIG. 6B shows a concentration distribution of the sample fluid over a sensing element 14 having twelve electrodes 20a-20l at 1 second (just prior to the first pulse). FIG. 6C shows a concentration distribution of the sample fluid over the sensing element 14 at 20 seconds (just prior to the second pulse). FIG. 6D shows a concentration distribution of the sample fluid over the sensing element 14 at 45 seconds (just after the third pulse). FIG. 6E shows a concentration distribution of the sample fluid over the sensing element 14 at 90 seconds (just after the fifth pulse). FIG. 6F shows a concentration distribution of the sample fluid over the sensing element 14 at 145 seconds (well after the fifth pulse). In the simulations, water with a known sodium content can be used as the sample fluid is used. The sodium concentration in the sample fluid can be about 250 mol/m$^3$. The sodium concentration of the calibration fluid used in the simulations can be about 40 mol/m$^3$. In a real measurement case, a concentration of certain constituent(s) in the sample fluid may be unknown and a concentration of certain constituent(s) in the calibration fluid is known. The total amount of the sample fluid used in the simulations is twice the volume of the sensing channel 22.

FIGS. 6A and 6B show that at 1 second (immediately after the first pulse), the calibration fluid is replaced with the sample fluid partially over the first three electrodes 20a-20c with relatively high concentration. FIGS. 6A and 6C show that at 20 seconds (immediately before the second pulse), the calibration fluid is replaced with the sample fluid partially over the first seven electrodes 20a-20g with a sample concentration (sodium in this example) lower than the concentration in FIG. 6B. FIG. 6C indicates that, over time, the sample fluid diffuses into the calibration fluid. FIGS. 6A and 6D show that at 45 seconds (immediately after the third pulse), the calibration fluid is replaced with the sample fluid partially over the eight electrodes 20a-20h with a relatively high concentration. FIGS. 6A and 6E show that at 90 seconds (shortly after the fifth pulse), the concentration of the sample fluid is relatively high over the twelve electrodes 20a-20l. FIGS. 6A and 6F show that at 145 seconds (about 60 seconds after the fifth pulse), the concentration of the sample fluid is even higher than the concentration of FIG. 6E.

Figures 7A, 7B:
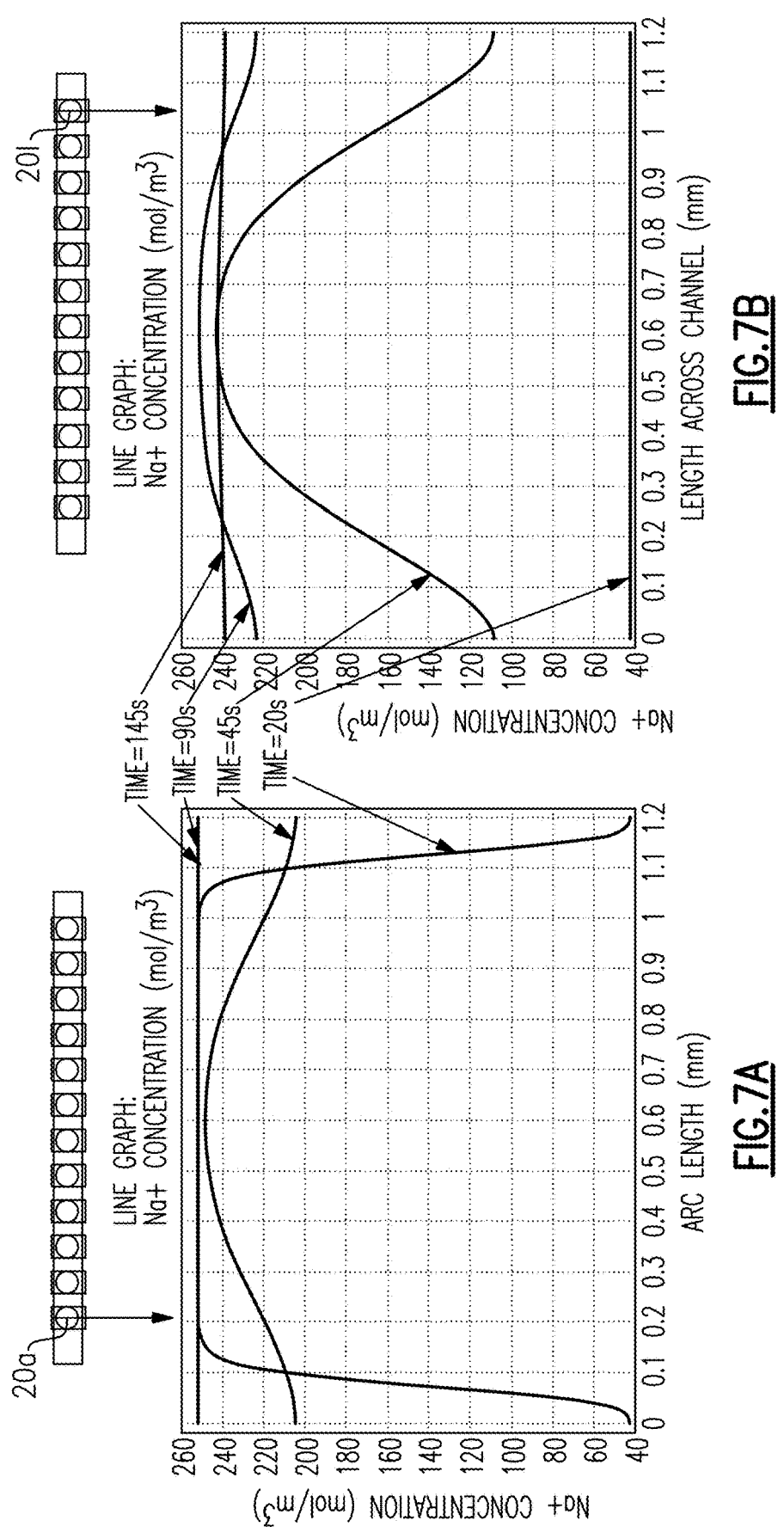
FIG. 7A shows the sodium concentration over a surface of an electrode at various time periods.
FIG. 7B shows the sodium concentration over a surface of another electrode at various time periods.
Figure 8B:
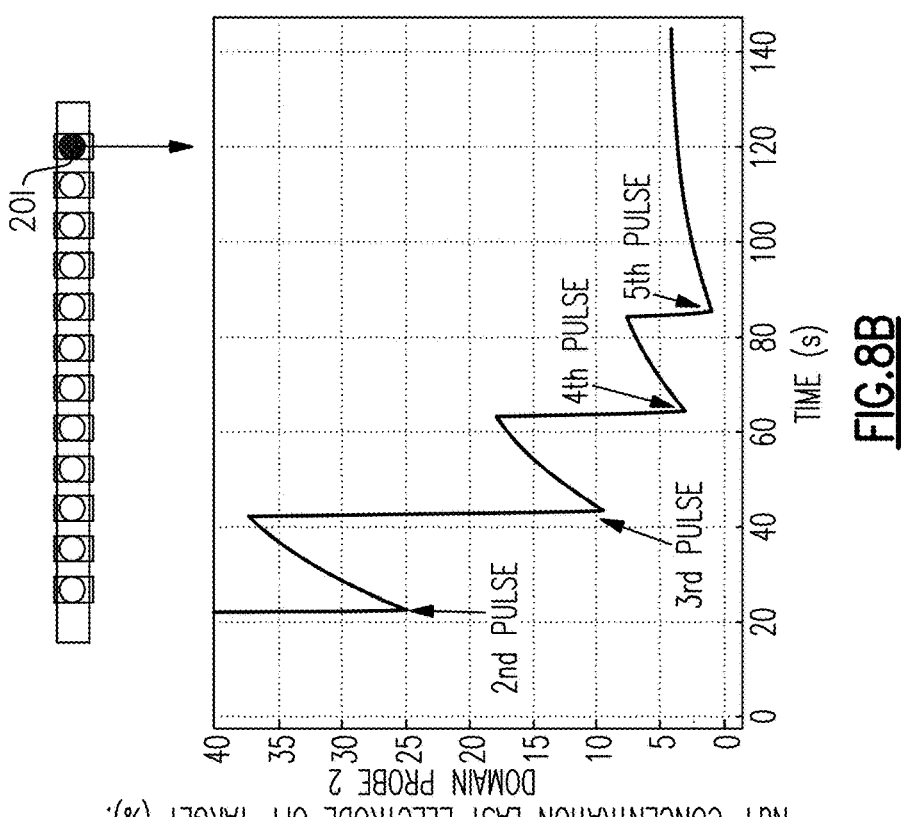
FIG. 8B shows an average concentration of the calibration fluid over a surface of another electrode measured over time.
Figure 8A:
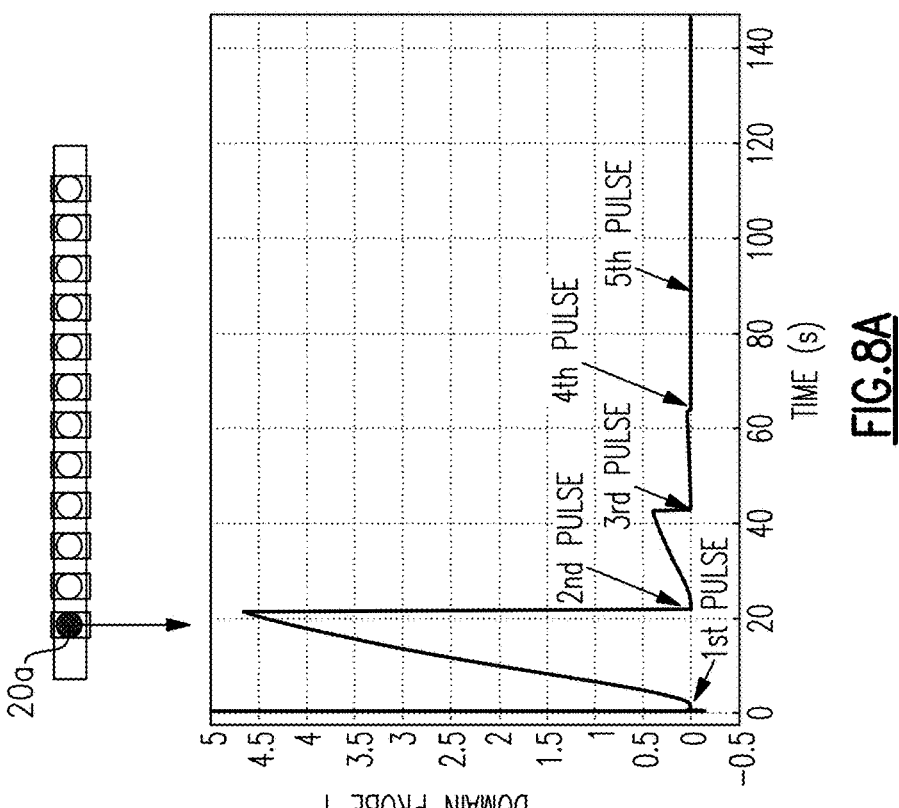
FIG. 8A shows an average concentration of the calibration fluid over a surface of an electrode measured over time.
Figure 8D:
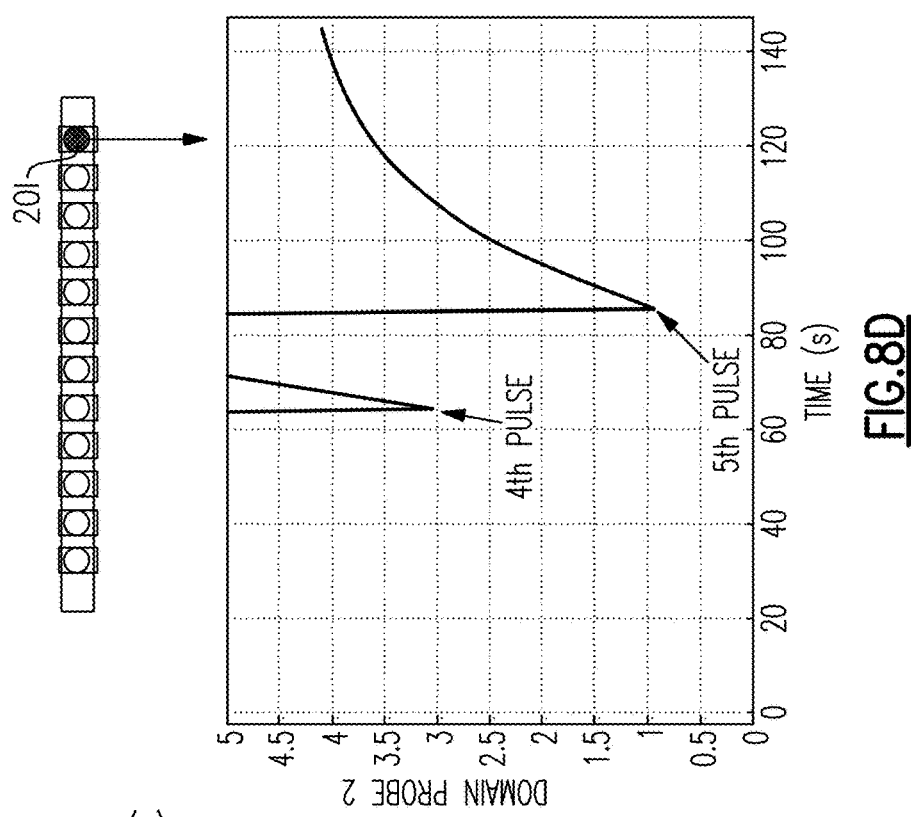
FIGS. 8C and 8D are enlarged views of FIGS. 8A and 8B, respectively, over smaller concentration scales of the y-axes.
Figure 8C:
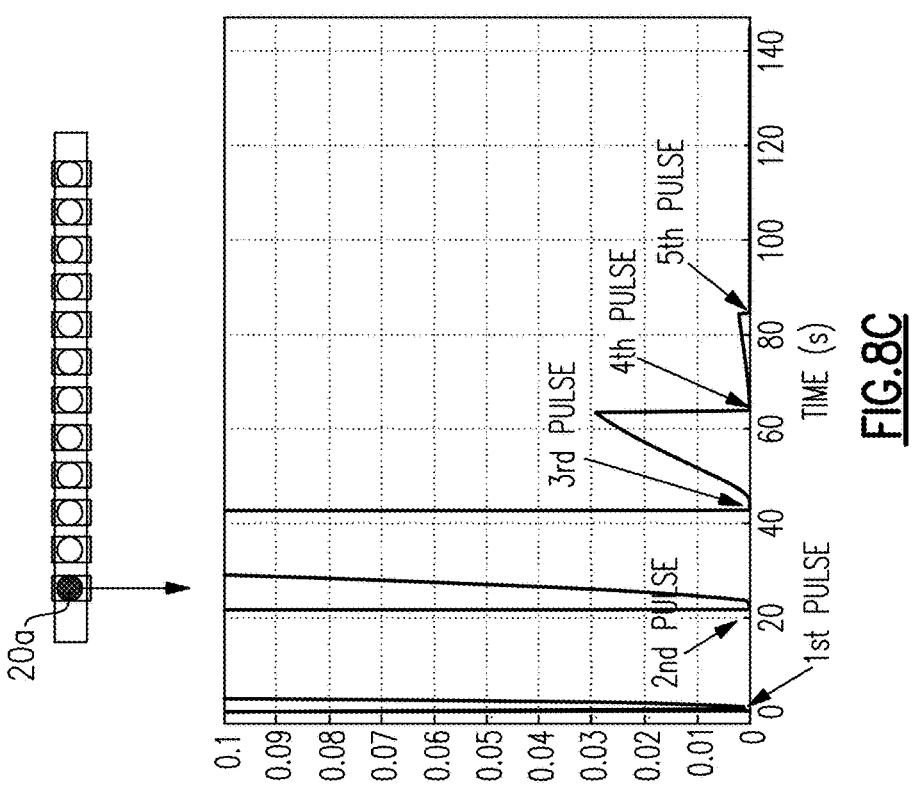

FIG. 7A shows the sodium concentration over a surface of the first electrode 20a (near an upstream end of the sensing channel 22) measured at 20 seconds, 45, seconds, 90 seconds, and 145 seconds in the simulation of FIGS. 6A-6F. FIG. 7B shows the sodium concentration over a surface of the twelfth electrode 20l (near a downstream end of the sensing channel 22) measured at 20 seconds, 45, seconds, 90 seconds, and 145 seconds in the simulation of FIGS. 6A-6F. FIG. 8A shows an average concentration of the calibration fluid over a surface of the first electrode 20a measured over time. FIG. 8B shows an average concentration of the calibration fluid over a surface of the twelfth electrode 20l measured over time. FIGS. 8C and 8D are zoomed-in views of portions of FIGS. 8A and 8B.

FIGS. 7A and 7B shows that the concentration of the sample fluid (the sodium concentration in the present example) reaches close to 100% (about 250 mol/m³ in the present example) at the first electrode 20a relatively quickly, and the concentration of the sample fluid reaches close to 100% at the twelfth electrode 20l at a slower rate. FIGS. 8A-8D shows that the average concentration of the calibration fluid reaches close to zero relatively quickly, and the concentration of the sample fluid reaches close to zero at the twelfth electrode 20l at a slower rate.

Figures 9A, 9B, 9C, 9D:
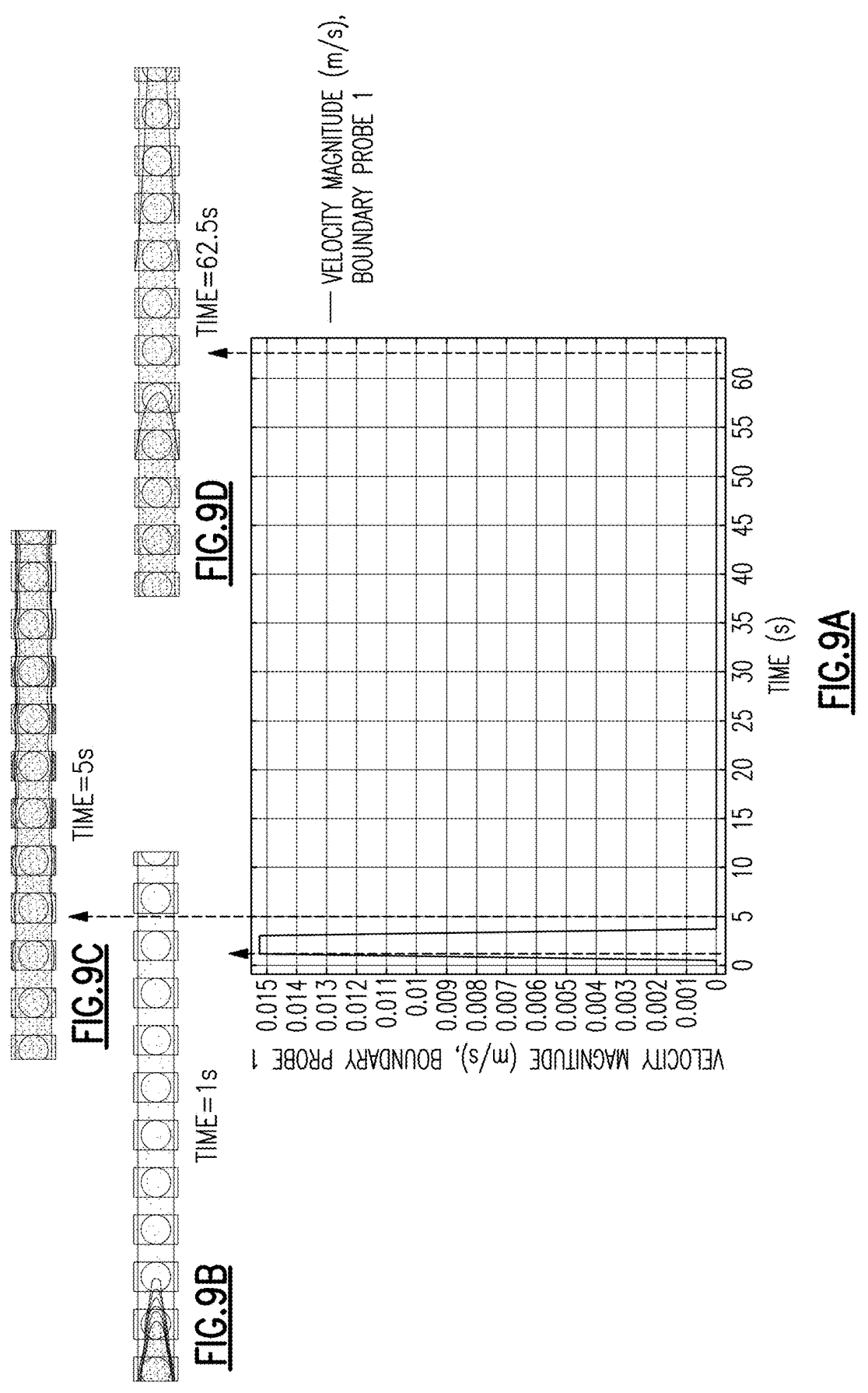
FIG. 9A is a graph showing three simulation time periods during exchange of a particular fluid with an existing fluid using a single pule.
FIGS. 9B-9D show concentration distributions of the particular fluid over a sensing element at various time periods.

FIG. 9A is a graph showing three simulation time periods during exchange of a particular fluid (e.g., the sample fluid) with an existing fluid (e.g., the calibration fluid) using a single pulse. FIG. 9B shows a concentration distribution of the sample fluid over a sensing element 14 having twelve electrodes 20a-20l at 1 second (just before the single pulse). FIG. 9C shows a concentration distribution of the sample fluid over the sensing element 14 at 5 seconds (just after the single pulse). FIG. 9D shows a concentration distribution of the sample fluid over the sensing element 14 at 62.5 seconds (well after the single pulse). In the simulations, water with a known sodium content can be used as the sample fluid is used. For the purposes of simulations. the sodium concentration in the sample fluid can be about 250 mol/m³, and the sodium concentration in the calibration fluid can be about 40 mol/m³. The amount of the sample fluid used in the single pulse is twice the volume of the sensing channel 22 (the same amount as the total amount of the sample fluid used in the five-pulse simulations of FIGS. 6A-8D).

Figures 10A, 10B:
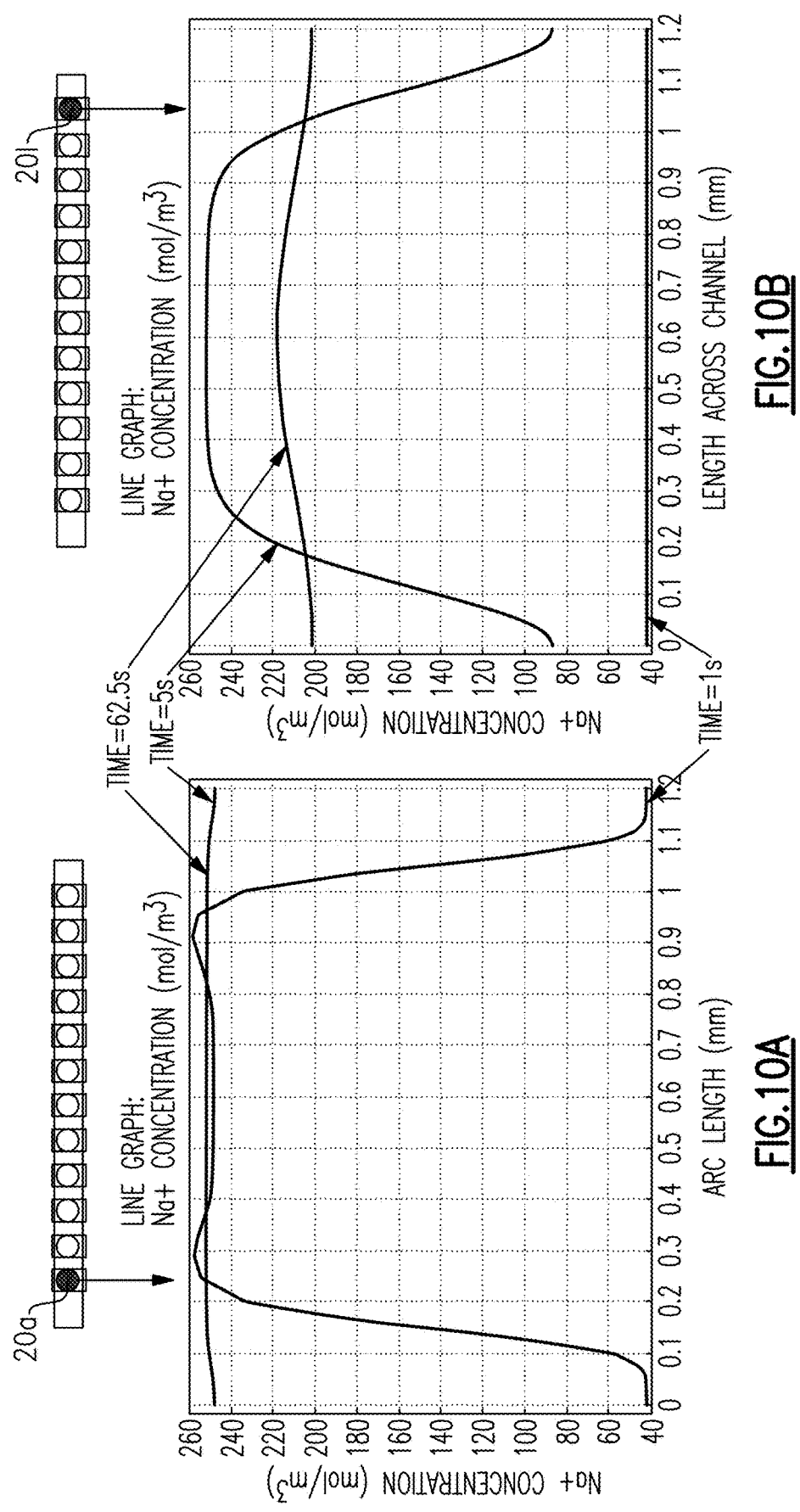
FIG. 10A shows a sodium concentration over a surface of a first electrode measured at 1 second, 5 seconds, and 62.5 seconds in the simulation of FIGS. 9A-9D.
FIG. 10B shows a sodium concentration over a surface of a twelfth electrode a measured at 1 second, 5 seconds, and 62.5 seconds in the simulation of FIGS. 9A-9D.
Figure 11B:
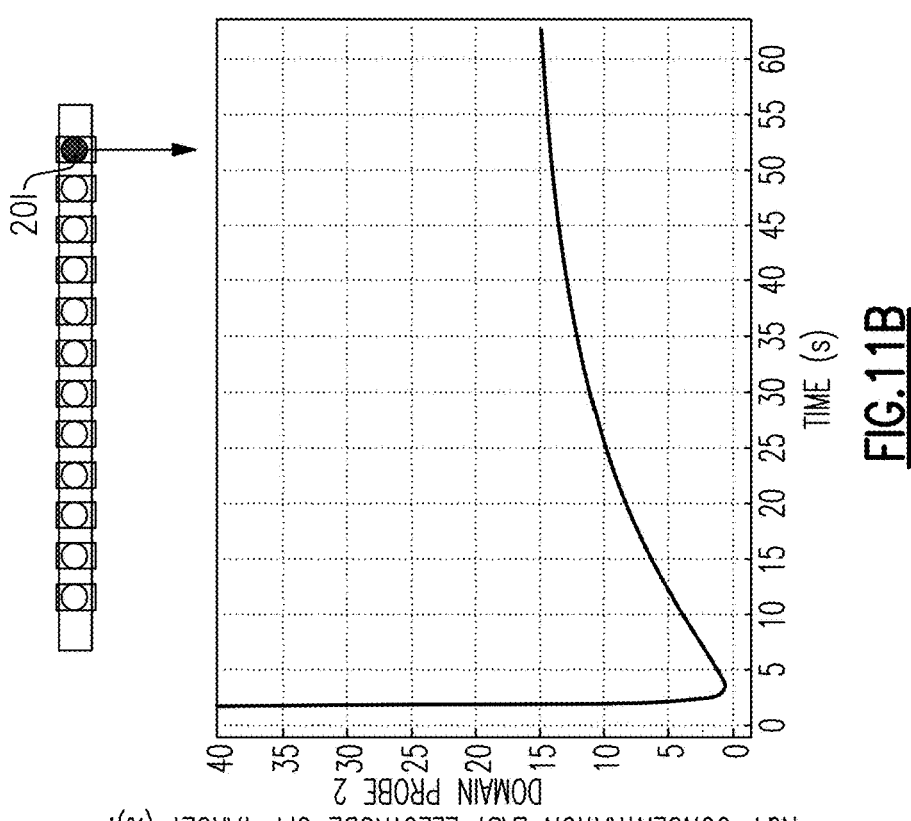
FIG. 11B shows an average concentration of a calibration fluid over a surface of the twelfth electrode of the series of electrodes measured over time.
Figure 11A:
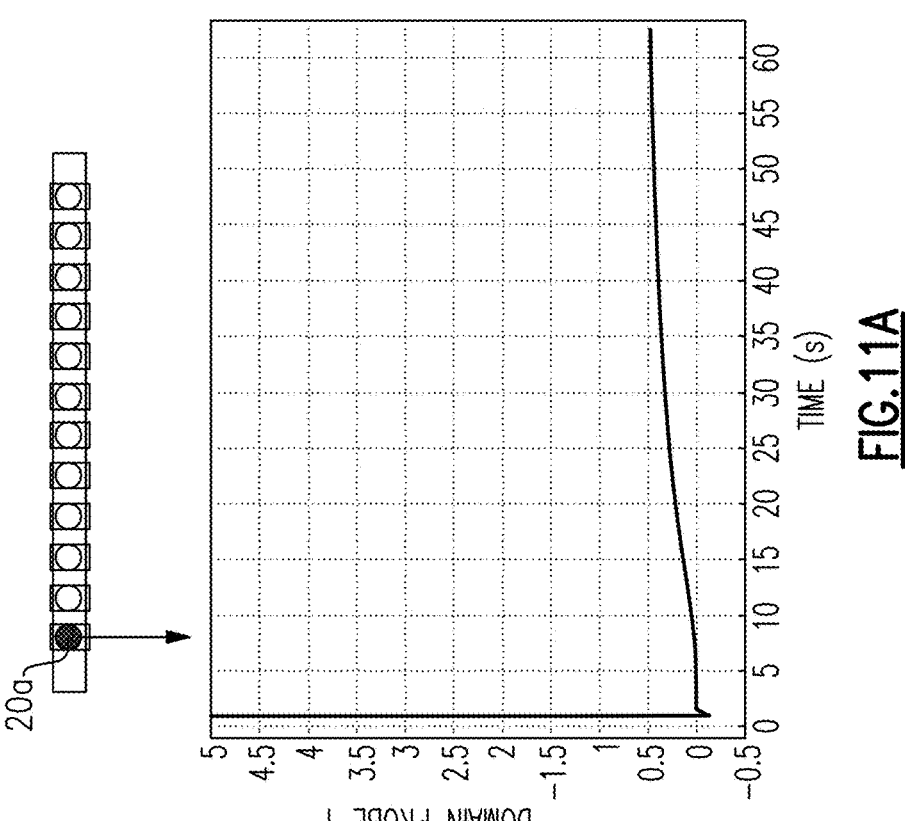
FIG. 11A shows an average concentration of a calibration fluid over a surface of the first electrode of a series of electrodes measured over time.

FIG. 10A shows the sodium concentration over a surface of the first electrode 20a measured at 1 second, 5, seconds, and 62.5 seconds in the simulation of FIGS. 9A-9D. FIG. 10B shows the sodium concentration over a surface of the twelfth electrode 20l measured at 1 second, 5, seconds, and 62.5 seconds in the simulation of FIGS. 9A-9D. FIG. 11A shows an average concentration of the calibration fluid over a surface of the first electrode 20a measured over time. FIG. 11B shows an average concentration of the calibration fluid over a surface of the twelfth electrode 20l measured over time.

Figure 12B:
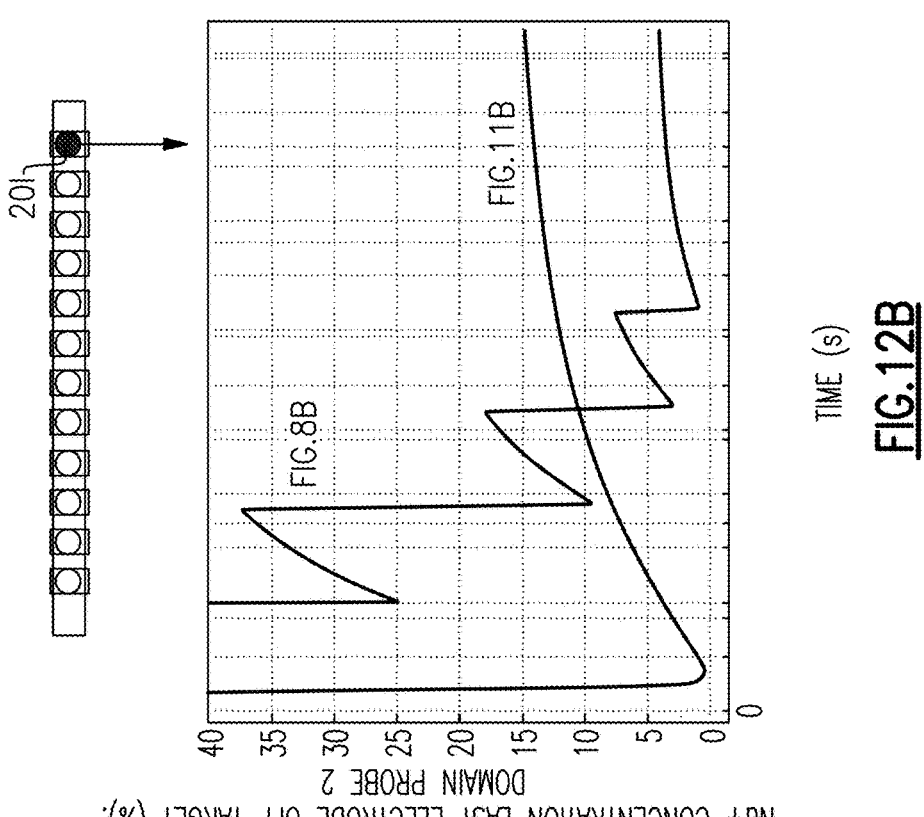
FIG. 12B combines the simulations results of FIGS. 8B and 11B.
Figure 12A:
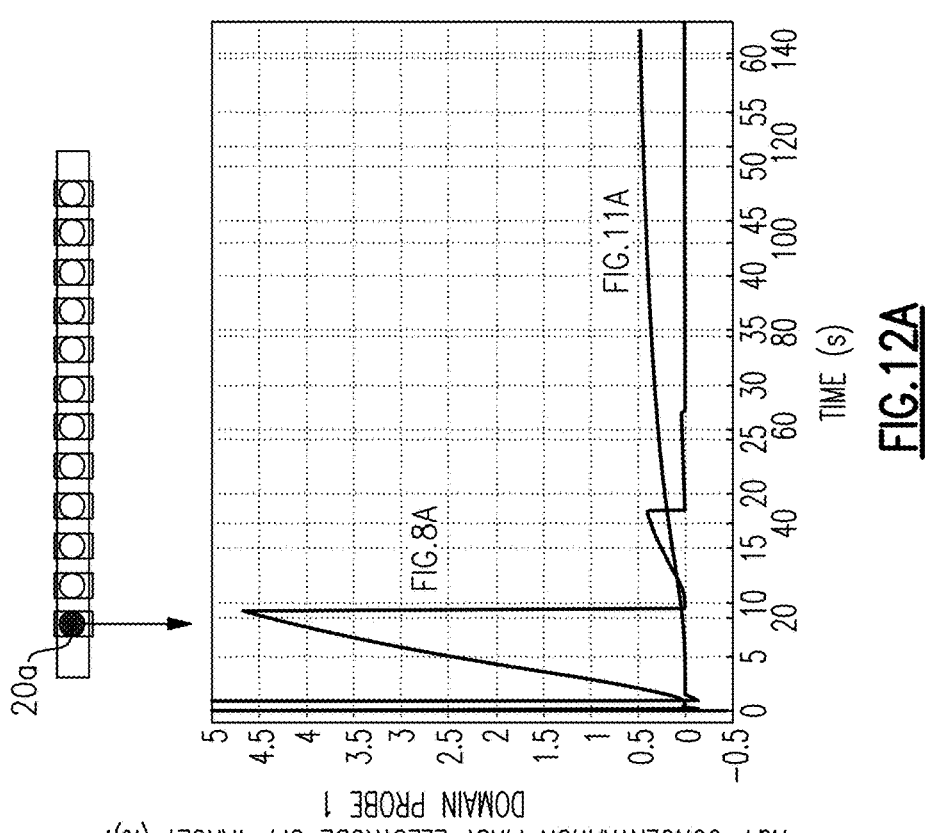
FIG. 12A combines the simulations results of FIGS. 8A and 11A.

FIG. 12A combines the simulations results of FIGS. 8A and 11A. FIG. 12B combines the simulations results of FIGS. 8B and 11B. FIGS. 12A and 12B indicate that it can be more difficult to replace fluid in a channel for the electrodes positioned downstream in the sensing channel 22. FIGS. 12A and 12B also indicate that single pulse may provide about 15% error in measurement and multiple pulses can provide less than about 5% error, even though the total volume of sample fluid is the same in both single-pulse and multiple-pulse examples.

The calibration diffusion state 72 and/or the sample diffusion state 74 can provide sufficient time for the calibration fluid and/or the sample fluid to diffuse thereby improving the efficiency of the performance of the sensor module 10. For example, as compared to a single flush process, a five-flush process with 15 seconds in between each flush can result in up to about three times to thirteen times improvement of the final concentration accuracy. Also, in order to achieve the same final concentration accuracy, a multi-pulse process can use less amount of the fluid as compared to the single pulse process.

At or near each electrode of the first to twelfth electrodes 20a-20l, there can be non-uniformity, such as large scale surface roughness, crevices, pockets, etc., due to, for example, its manufacturing process. Such non-uniformities can interrupt fluid replacement in the sensing channel 22. In some embodiments, the advantages disclosed herein can be pronounced when the shape, profile, or geometry of the sensing channel deviates from an ideal circular pipe.

Figure 13:
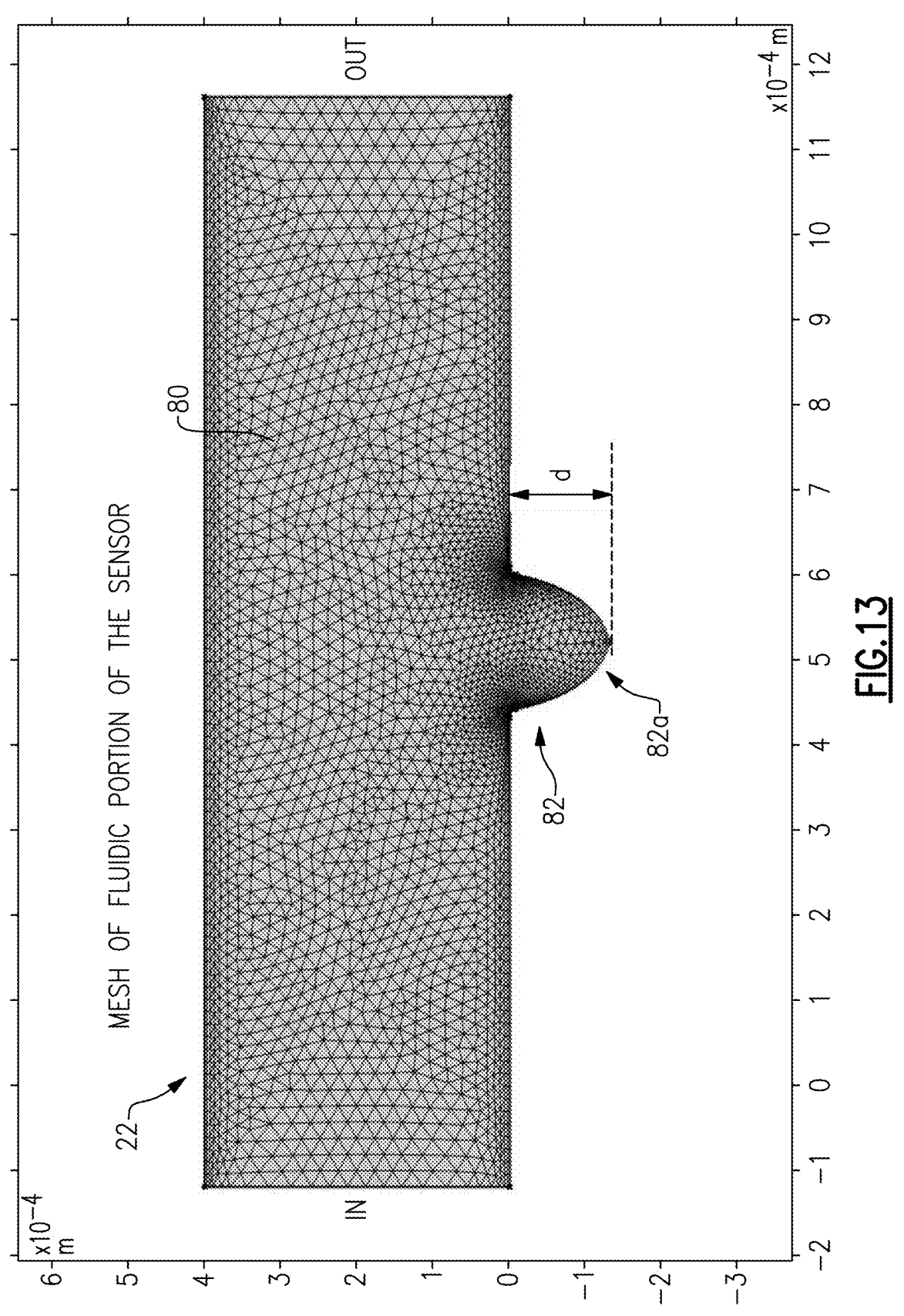
FIG. 13 shows a mesh illustration of a fluid in a cross-sectional side view of a portion of a sensing channel near a sensing element.

FIG. 13 shows a mesh illustration of a fluid 80 in a cross-sectional side view of a portion of a sensing channel near a sensing element (e.g., an electrode). The sensing channel 22 can include a well 82. The portion of the sensing channel 22 can be positioned between an inlet valve and an outlet valve. A surface of the well 82 can comprise a sensing surface 82a. In some embodiments, a depth d of the well 82 can be in a range between 50 μm and 250 μm. For example, the depth d of the well 82 can be in a range between 50 μm and 200 μm, between 100 μm and 250 μm, or between 100 μm and 200 μm. The fluid 80 can interact with the sensing element at the sensing surface 82a, and the sensing element can output a signal indicative of respective constituent components of the sample fluid. In some embodiments, the sample fluid can include calcium. In the sensing channel 22, the sample fluid may flow from an inlet side (IN) to an outlet side (OUT) with a generally laminar flow. In the simulations shown in FIGS. 14A-17E, a first fluid with calcium content of 1.165 mM is replaced with a second fluid with calcium content of 0.2 mM. The calcium content can be calculated based on voltage measured by the sensing element using static Nernst equation. Also, in the simulations shown in FIGS. 14A-17E, the depth d of the well 82 is set to 135 μm.

FIGS. 14A-14D are graphs showing simulation results including voltage sensed, velocity of fluid flow, calcium concentration, and exchange efficiency of a second fluid over time in a fluid exchange process using a continuous flow of the second fluid to replace the first fluid. FIGS. 15A-15D are graphs showing simulation results including voltage sensed, velocity of fluid flow, calcium concentration, and exchange efficiency of a second fluid over time in a fluid exchange process using a continuous flow of the second fluid for part of the time to replace the first fluid followed by a steady state of the second fluid for measurement. FIGS. 16A-16D are graphs showing simulation results of a fluid exchange process using a pulsed flow of a second fluid to replace a first fluid.

Figure 14A:
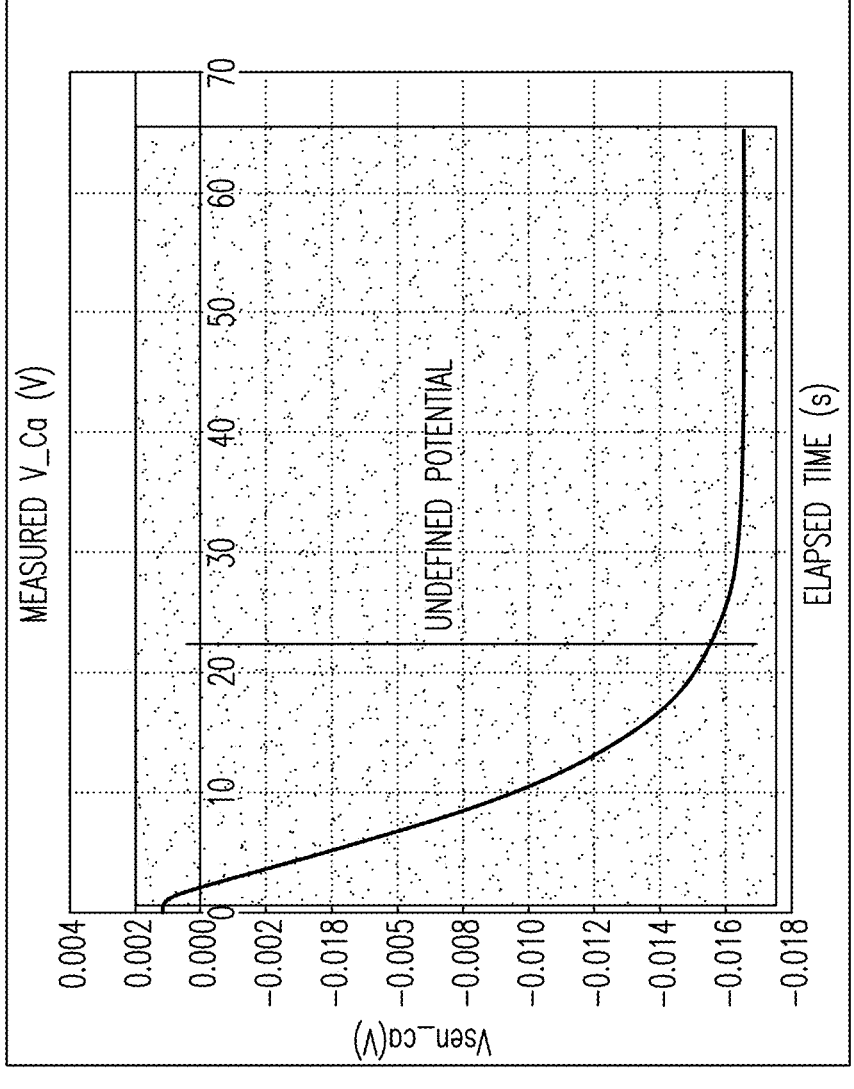
FIGS. 14A-14D are graphs showing simulation results including voltage sensed, velocity of fluid flow, calcium concentration, and exchange efficiency of a second fluid over time in a fluid exchange process using a continuous flow of the second fluid to replace a first fluid.
Figures 14B, 14C, 14D:
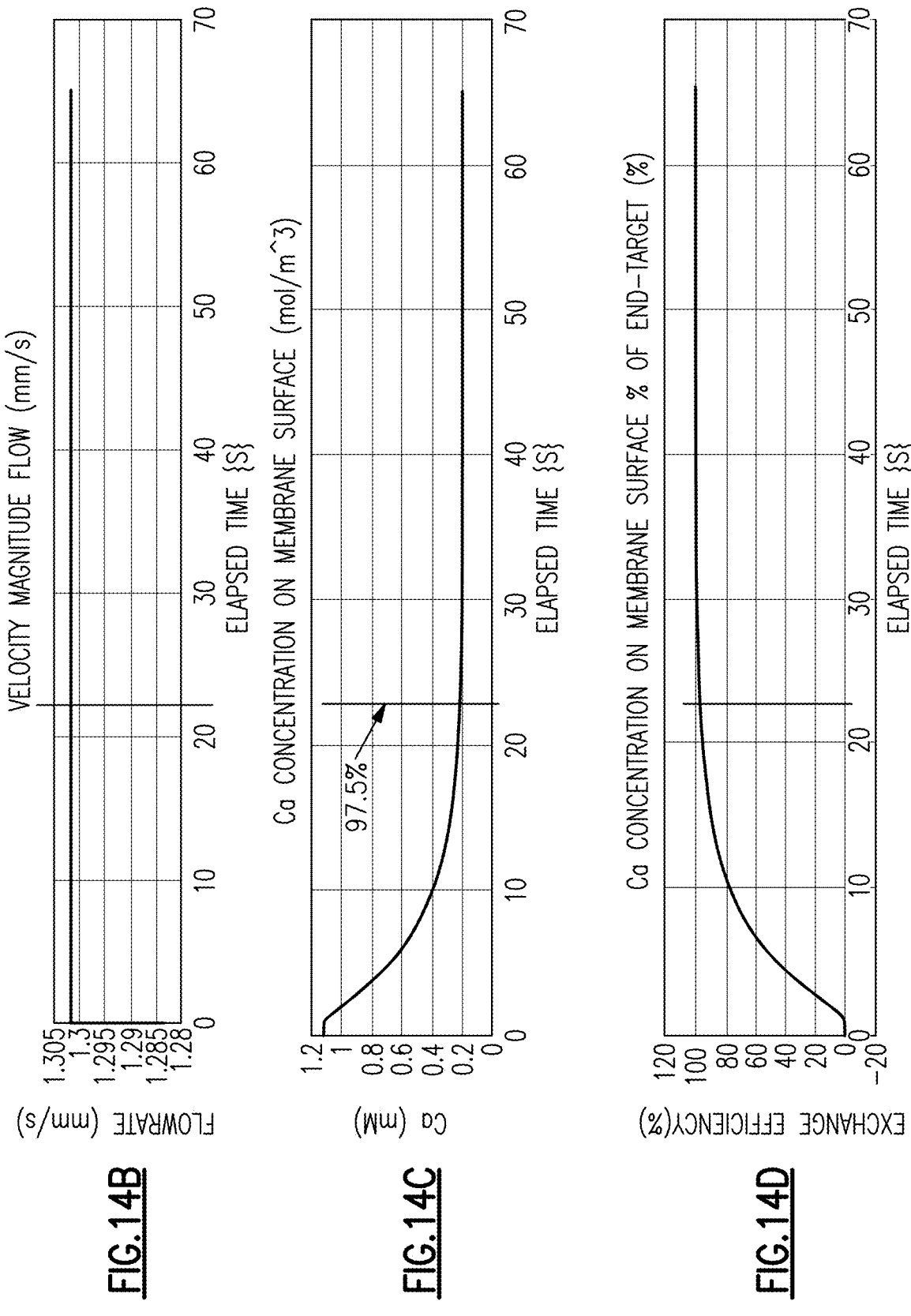

In the simulation of FIGS. 14A-14D, the second fluid is provided with a constant flow rate of about 1.302 mm/s. In the simulation of FIGS. 14A-14D there is no steady state of the second fluid for measurement. FIG. 14C indicates that, in order to reach 97.5% concentration change on the sensing surface 82a, a volume of the second fluid that is 22 times the volume of the sensing channel 22 is needed. Potential is undefined in the simulation of FIGS. 14A-14D, and is expected to vary with flow rates and geometry of the sensing channel 22. Accordingly, the simulation results indicate that the fluid exchange process using the continuous flow may not be reliable for accurate measurement.

Figure 15A:
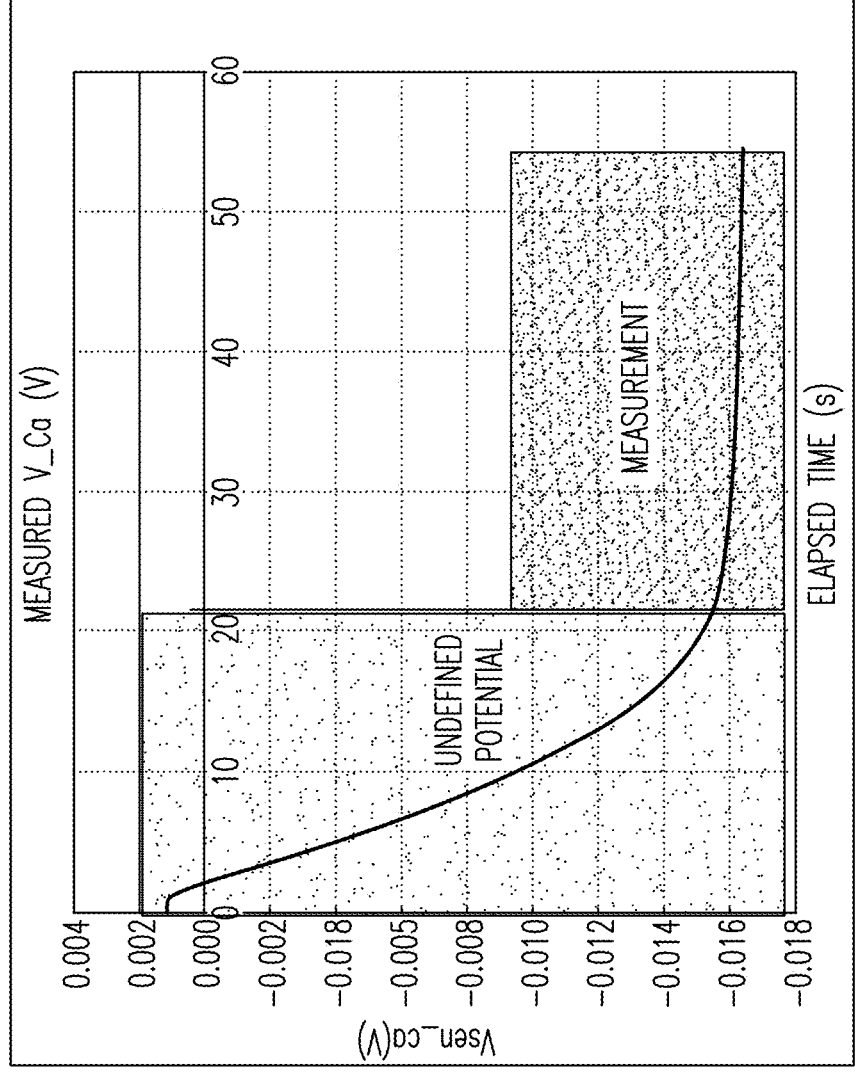
FIGS. 15A-15D are graphs showing simulation results including voltage sensed, velocity of fluid flow, calcium concentration, and exchange efficiency of a second fluid over time in a fluid exchange process using a continuous flow of the second fluid for part of the time to replace the first fluid followed by a steady state for measurement.
Figures 15B, 15C, 15D:
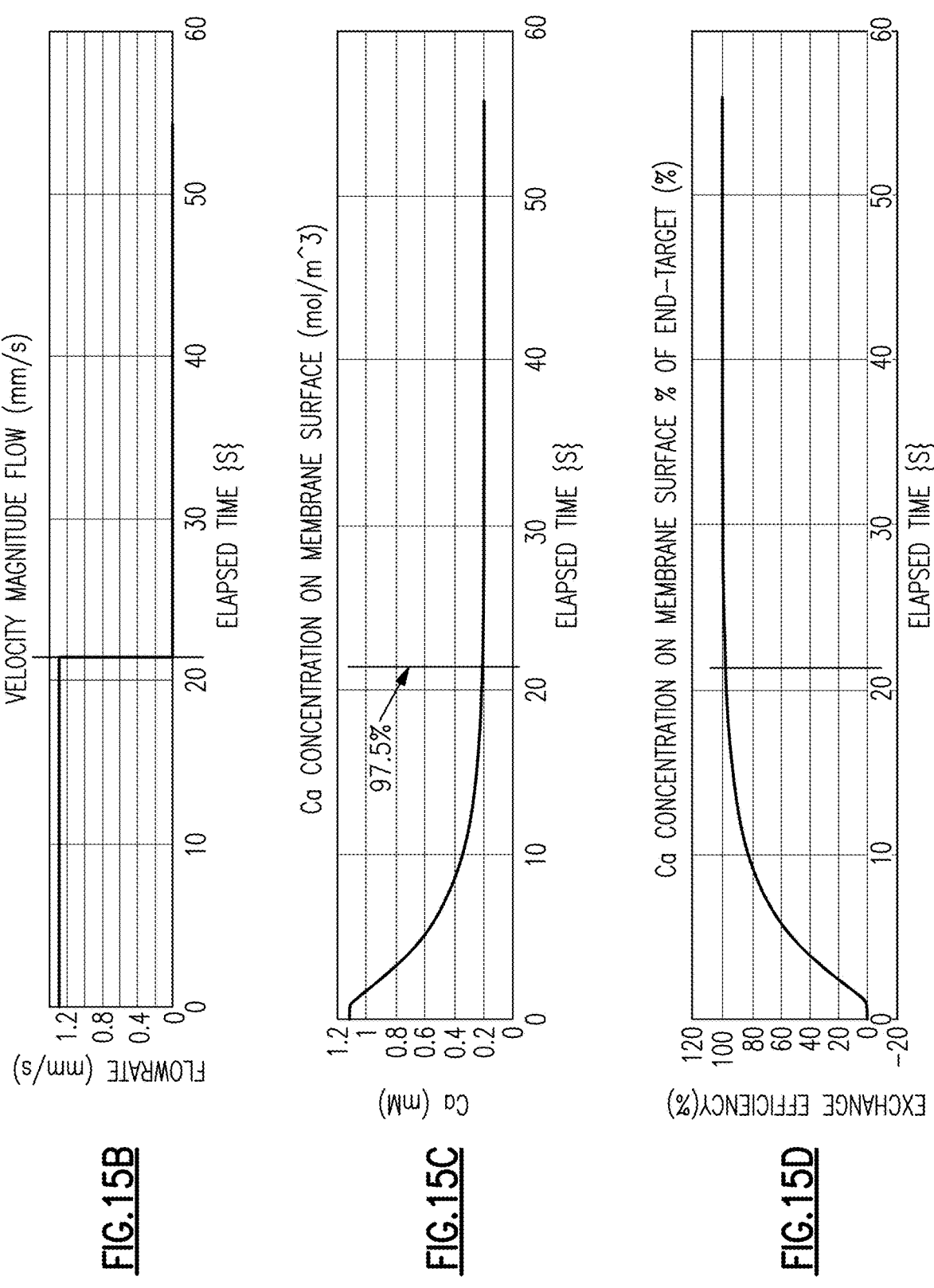

In the simulation of FIGS. 15A-15D, the second fluid is provided with a constant flow rate of about 1.302 mm/s until the concentration change on the sensing surface 82a reaches 97.5%. After providing the second fluid, measurement is made for 30 seconds. Unlike the simulation of FIGS. 14A-14D in which the second fluid is kept flowing after the concentration change on the sensing surface 82a reaches 97.5%, in the simulation of FIGS. 15A-15D the flow of the second fluid is stopped after the concentration change on the sensing surface 82a reaches 97.5% for measurement. FIG. 15C indicates that, in order to reach 97.5% concentration change on the sensing surface 82a, a volume of the second fluid that is 22 times the volume of the sensing channel 22 is needed. After the flow of the second fluid is terminated, the potential can be defined, and allows the sensing element to make accurate measurements.

Figure 16A:
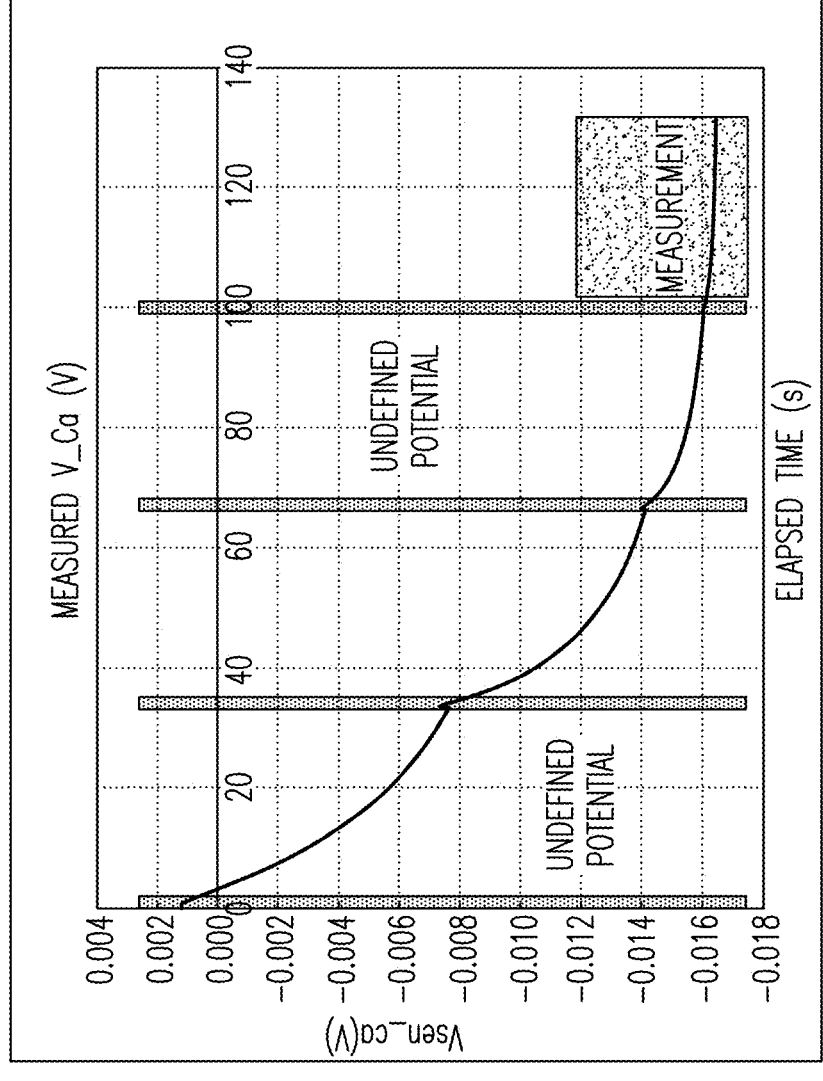
FIGS. 16A-16D are graphs showing simulation results including voltage sensed, velocity of fluid flow, calcium concentration, and exchange efficiency of a second fluid over time in a fluid exchange process using a pulsed flow of a second fluid to replace a first fluid.
Figures 16B, 16C, 16D:
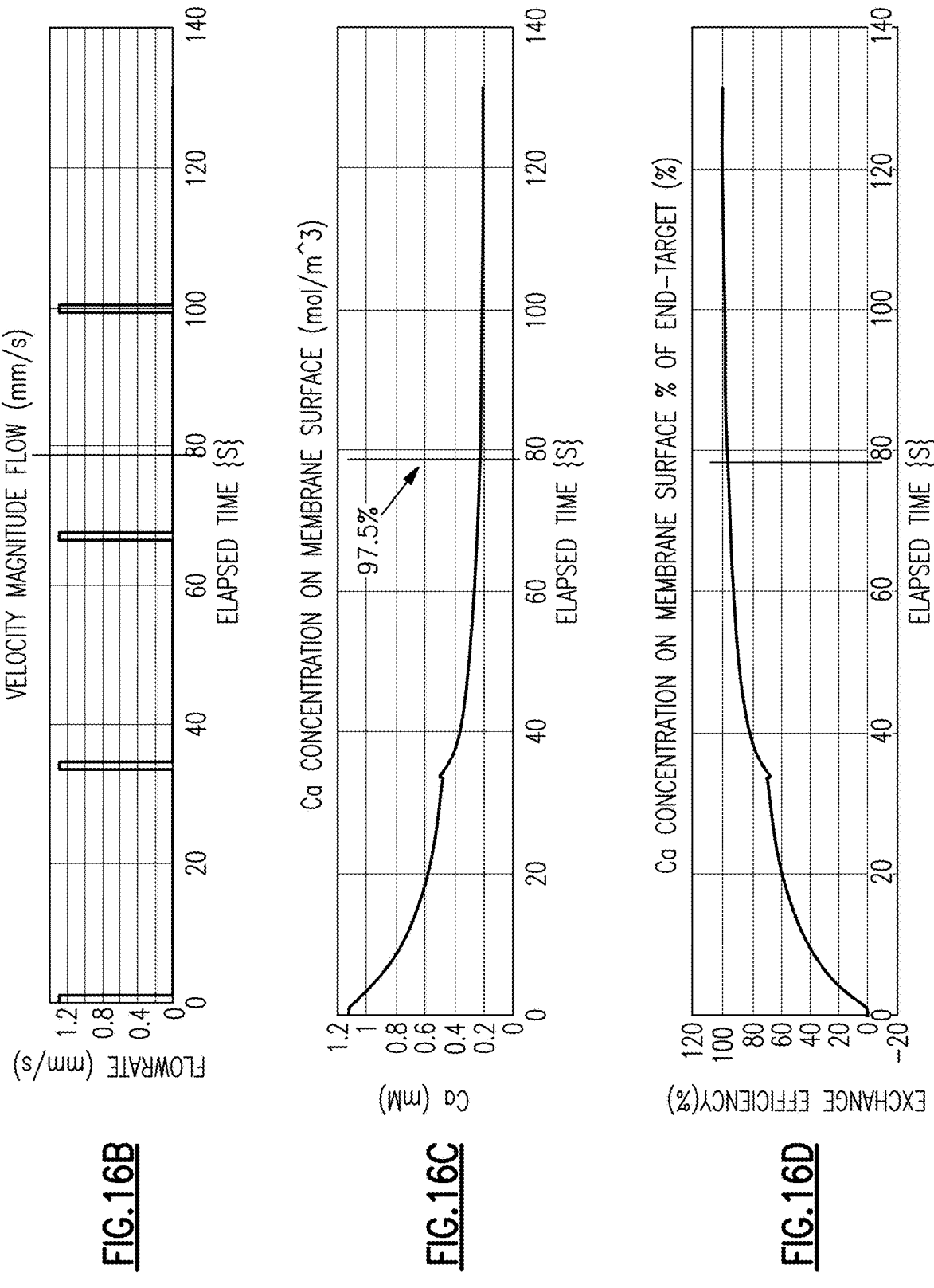

In the simulation of FIGS. 16A-16D, the second fluid is provided in four pulses or flushes with each pulse having a volume equal to the volume of the sensing channel. The approach used in the simulation of FIGS. 16A-16D can be referred to as an advection and diffusion approach. In the simulation, a single flush time of 1 second, and a soak time (a diffusion time) of 30 seconds after each flush are used. FIG. 16C indicates that, a volume of the second fluid that is merely 3 times the volume of the sensing channel 22 (that is, after 3 pulses) can enable the concentration change on the sensing surface 82a to be reach 97.5%. When the flow of the second fluid is stopped (that is, after each pulse), the potential can be defined, and allows the sensing element to make accurate measurements. For example, an accurate measurement can be taken after the fourth pulse of the second fluid. Because the concentration change reaches 97.5% after the third pulse, taking the measurement after the fourth pulse can ensure that the measurement is accurate.

The simulation results of FIGS. 14A-16D indicate that the fluid exchange process using a pulsed flow can significantly reduce the amount needed to enable the concentration change on the sensing surface 82a to be sufficiently high (e.g., 97.5%). In some applications, the concentration change of over 80%, over 85%, over 90%, or over 95% is considered sufficiently high for making an accurate measurement.

Figure 17A:
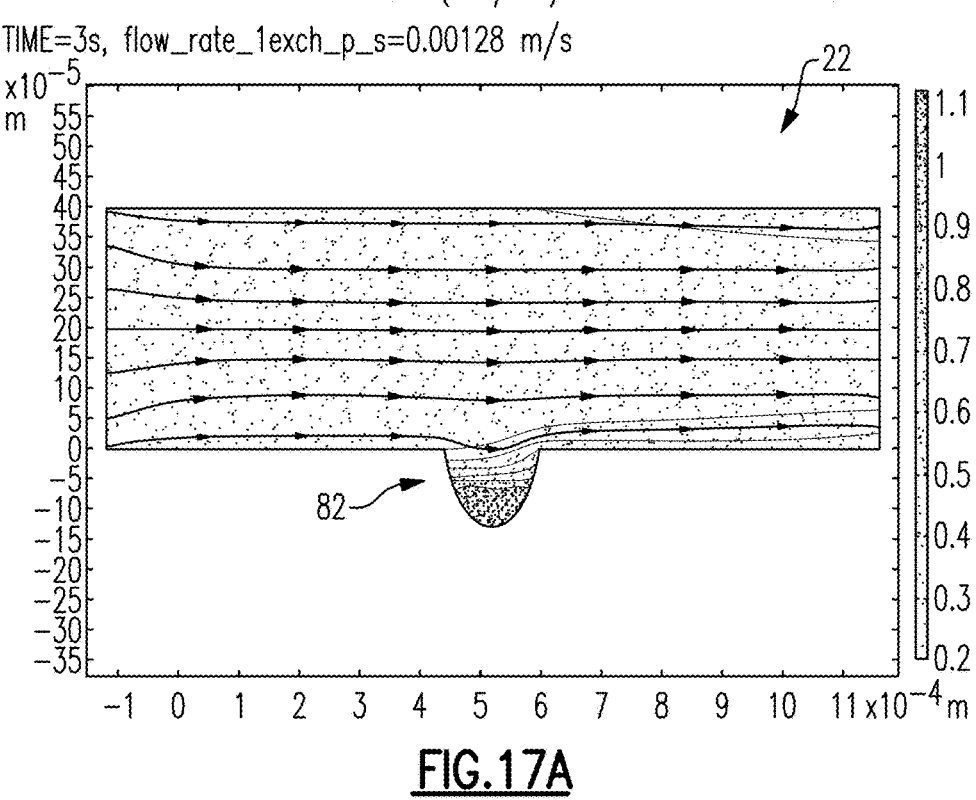
FIGS. 17A-17D illustrate concentration distribution and flow directions of the first and second fluid in a sensing channel.

FIGS. 17A-17D illustrate concentration distribution and flow or diffusion directions of the first and second fluid in the sensing channel 22. FIG. 17A shows the concentration distribution and flow directions of the first and second fluid in the sensing channel 22 during the first pulse in the simulation of FIGS. 16A-16D. A generally laminar flow of the second fluid can be seen in the sensing channel 22 in FIG. 17A. Also, a relatively high concentration of the first fluid can be observed in the well 82.

Figure 17B:
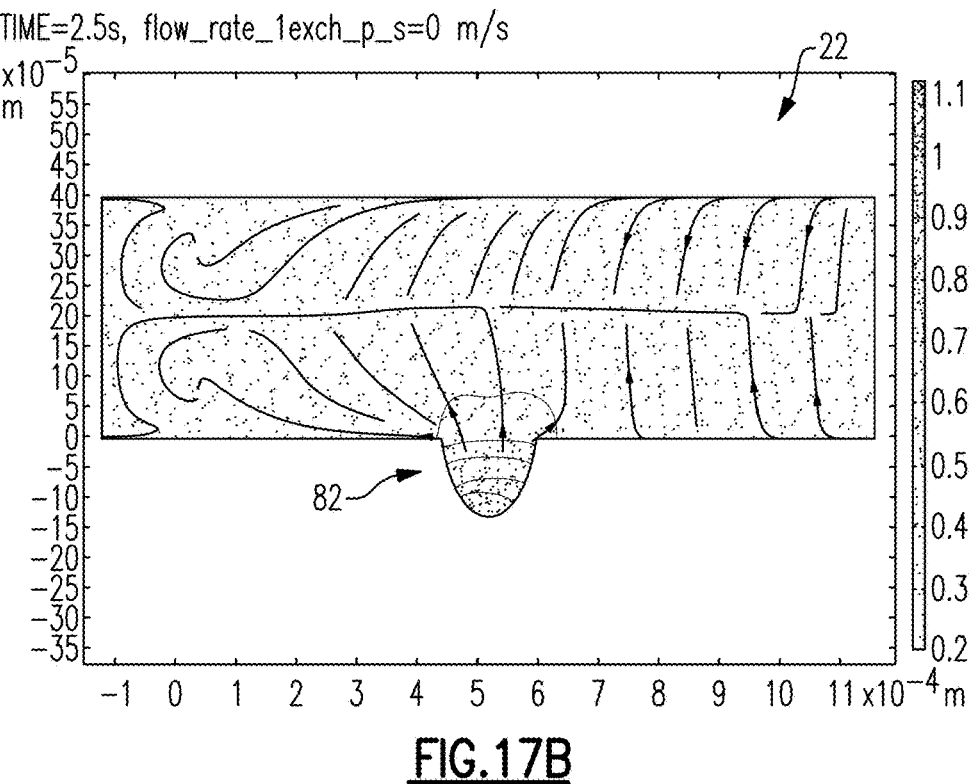
Figure 17C:
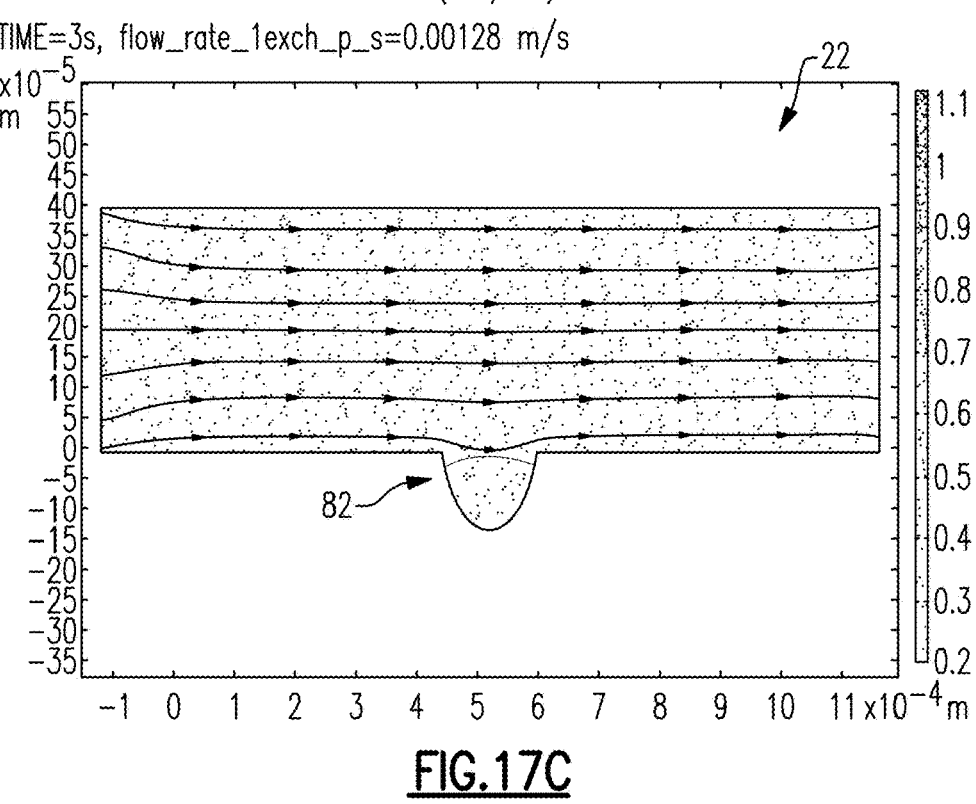
Figure 17D:
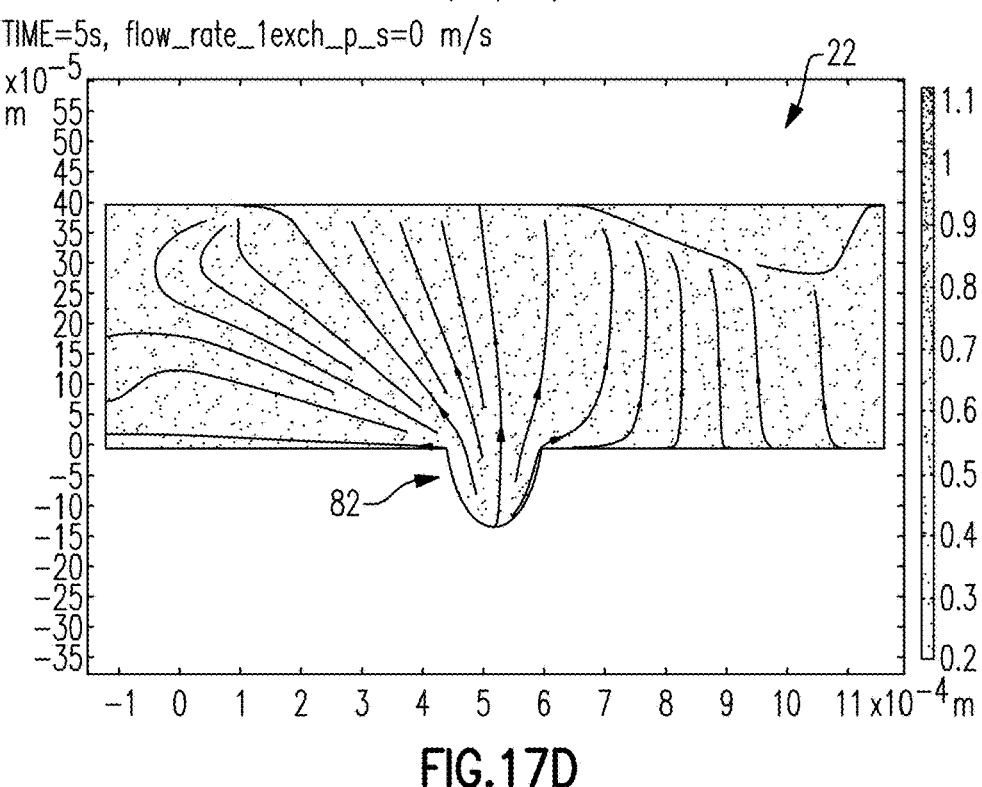

FIG. 17B shows the concentration distribution and diffusion directions of the first and second fluid in the sensing channel 22 during a diffusion period after the first pulse. In the diffusion period, diffusion can occur in the sensing channel 22 between the first and second fluids. The diffusion period can enable the first fluid in the well 82 to diffuse into the second fluid over the well 82. In FIGS. 17C and 17B, another pulse and diffusion period can be repeated to achieve higher concentration of the second fluid in the sensing channel 22.

Figure 18A:
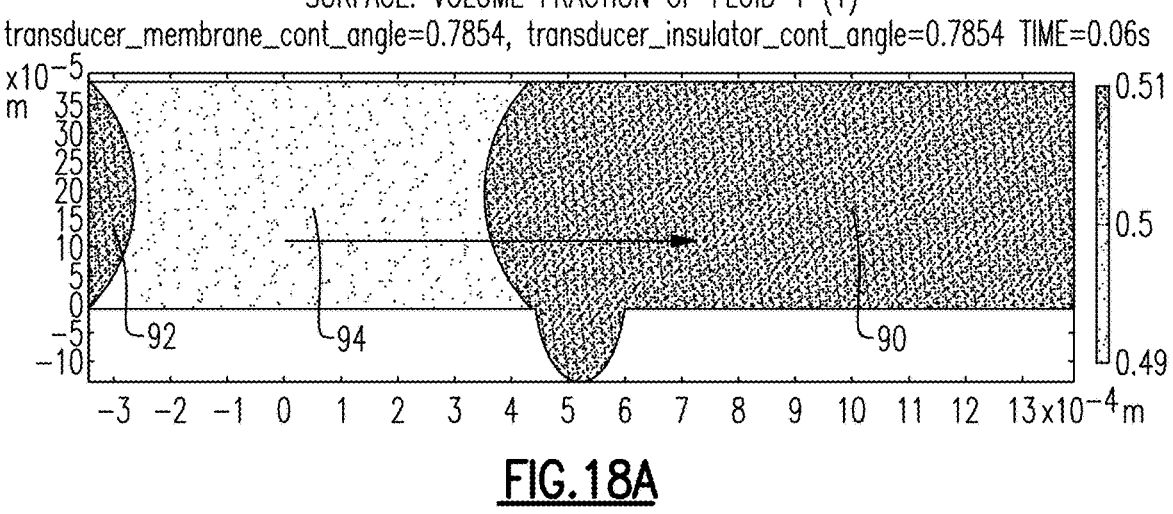
FIGS. 18A-18C schematically illustrate a process of replacing a first fluid with a second fluid using an air segment therebetween.
Figure 18B:
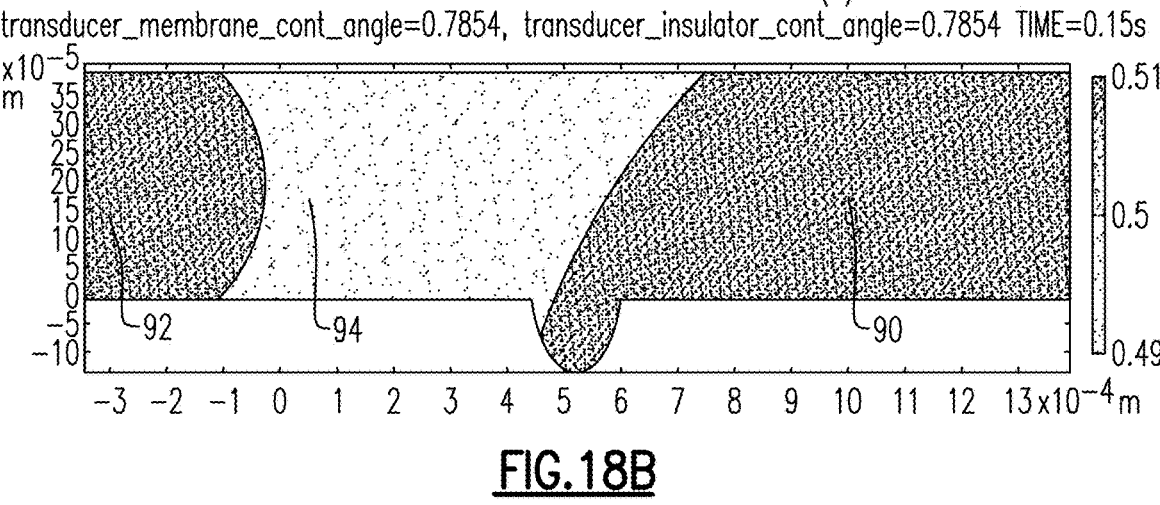
Figure 18C:
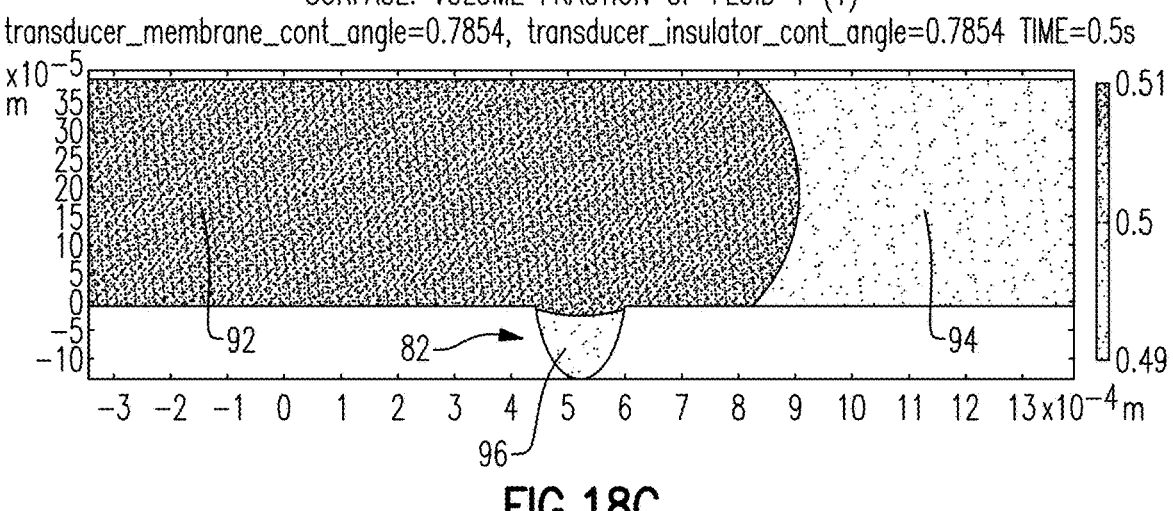

FIGS. 18A-18C schematically illustrate a process of replacing a first fluid 90 with a second fluid 92 using an air segment 94 therebetween. As shown in FIG. 18C, an air pocket 96 may be formed in the well 82.

Figure 18D:
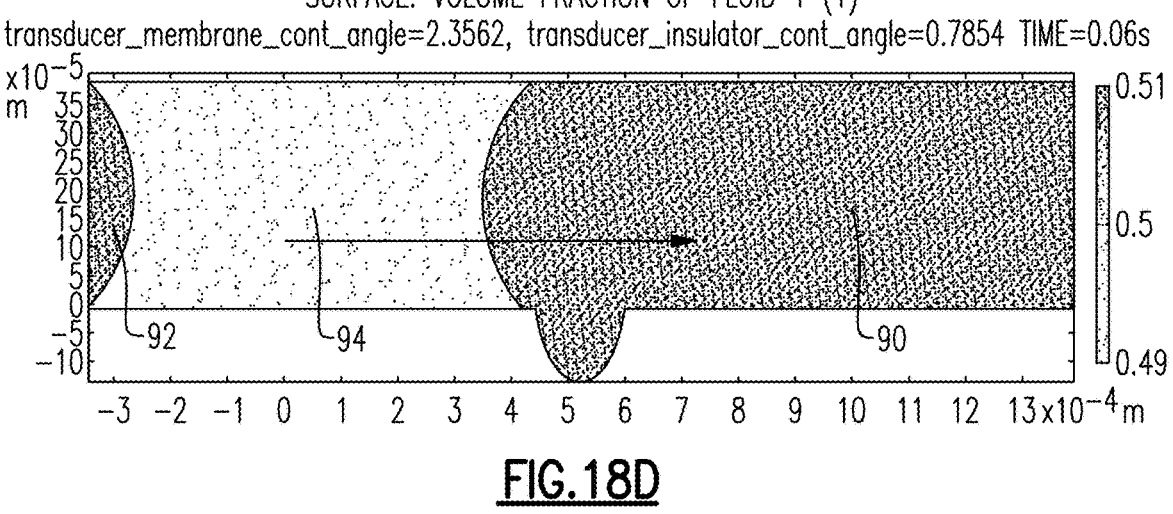
FIGS. 18D-18F schematically illustrate another process of replacing a first fluid with a second fluid using an air segment therebetween.
Figure 18E:
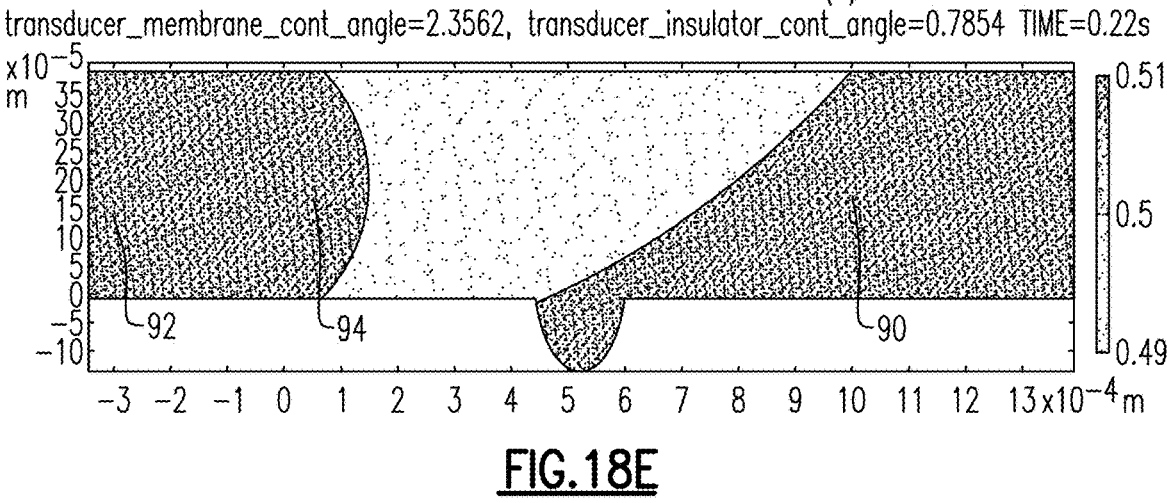
Figure 18F:
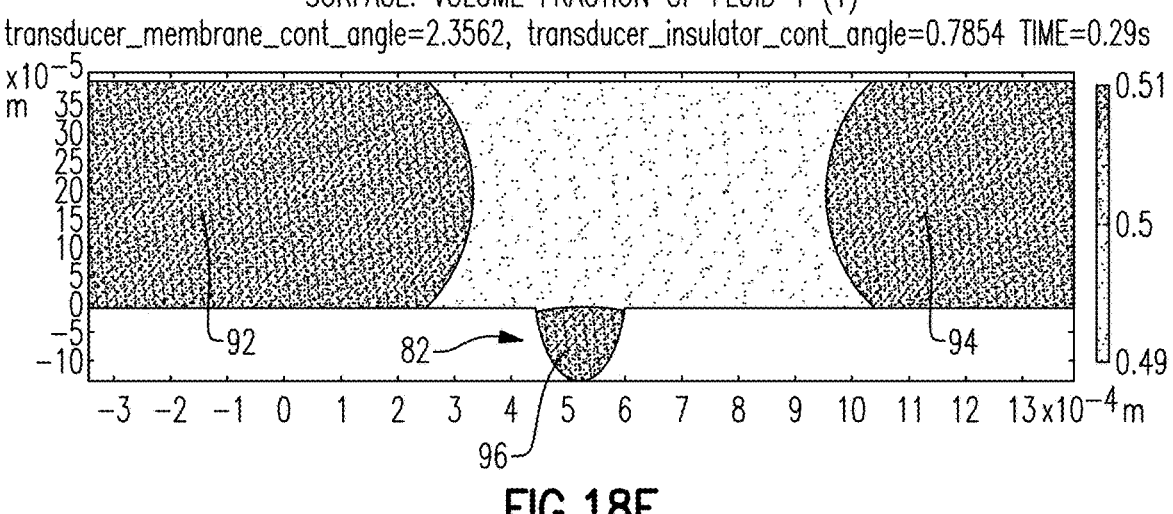

FIGS. 18D-18F schematically illustrate another process of replacing a first fluid 90 with a second fluid 92 using an air segment 94 therebetween. As shown in FIG. 19C, a trapped first fluid portion 98 may be formed in the well 82.

Though using air to aid replacement of the first fluid with the second fluid can be beneficial as air may be easily accessible and it would not consume the second fluid or reduce the amount of second fluid for the replacement, due to the defects described with respect to FIGS. 18A-18F (the formation of the air pocket 96 or the trapped first fluid portion 98), it may not provide sufficient reliability. However, combinations of the air segment 94 and one or more fluid replacement method disclosed herein can enable a sufficiently reliable sensing process. For example, the use of the air segment 94 can be combined with the process described with respect to FIGS. 15A-15D and/or the process described with respect to FIGS. 16A-16D.

Though the pulsed supply of the sample fluid is mainly discussed herein, the principles and advantages disclosed herein can be used to supply any suitable fluid to replace an existing fluid in a sensing channel. For example, the calibration fluid can be provided in a plurality of pulses to replace a sample fluid in the manner described above with respect to the reverse replacement.

Unless the context clearly requires otherwise, throughout the description and the claims, the words "comprise," "comprising," "include," "including" and the like are to be construed in an inclusive sense, as opposed to an exclusive or exhaustive sense; that is to say, in the sense of "including, but not limited to." The word "coupled", as generally used herein, refers to two or more elements that may be either directly connected, or connected by way of one or more intermediate elements. Likewise, the word "connected", as generally used herein, refers to two or more elements that may be either directly connected, or connected by way of one or more intermediate elements. Additionally, the words "herein," "above," "below," and words of similar import, when used in this application, shall refer to this application as a whole and not to any particular portions of this application. Moreover, as used herein, when a first element is described as being "on" or "over" a second element, the first element may be directly on or over the second element, such that the first and second elements directly contact, or the first element may be indirectly on or over the second element such that one or more elements intervene between the first and second elements. Where the context permits, words in the above Detailed Description using the singular or plural number may also include the plural or singular number respectively. The word "or" in reference to a list of two or more items, that word covers all of the following interpretations of the word: any of the items in the list, all of the items in the list, and any combination of the items in the list.

Moreover, conditional language used herein, such as, among others, "can," "could," "might," "may," "e.g.," "for example," "such as" and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments.

While certain embodiments have been described, these embodiments have been presented by way of example only, and are not intended to limit the scope of the disclosure. Indeed, the novel apparatus, methods, and systems described herein may be embodied in a variety of other forms; furthermore, various omissions, substitutions and changes in the form of the methods and systems described herein may be made without departing from the spirit of the disclosure. For example, while blocks are presented in a given arrangement, alternative embodiments may perform similar functionalities with different components and/or circuit topologies, and some blocks may be deleted, moved, added, subdivided, combined, and/or modified. Each of these blocks may be implemented in a variety of different ways. Any suitable combination of the elements and acts of the various embodiments described above can be combined to provide further embodiments. The accompanying claims and their equivalents are intended to cover such forms or modifications as would fall within the scope and spirit of the disclosure.

What is claimed is:

1. A method of operating a fluid sensing system, the method comprising:

prior to sensing a sample fluid in a sensing channel by a sensing element:

providing a first portion of the sample fluid in the sensing channel;

holding the first portion of the sample fluid in the sensing channel for a first diffusion period;

after the first diffusion period, providing a second portion of the sample fluid in the sensing channel; and holding the second portion of the sample fluid in the sensing channel for a second diffusion period; and after the second diffusion period, sensing the sample fluid in the sensing channel by the sensing element.

2. The method of claim 1, further comprising calibrating the sensing element in the sensing channel using a calibration fluid.

3. The method of claim 2, wherein the calibration fluid is provided in the sensing channel in multiple pulses.

4. The method of claim 3, wherein the calibrating the sensing element further includes holding at least a portion of the calibration fluid for diffusion to occur.

5. The method of claim 2, wherein the calibrating the sensing element comprises providing the calibration fluid into 2-6 portions and providing the portions in sequence with diffusion periods therebetween.

6. The method of claim 1, further comprising providing a third portion of the sample fluid in the sensing channel after the first diffusion period and before providing the second portion of the sample fluid, and holding the third portion of the sample fluid in the sensing channel for a third diffusion period.

7. The method of claim 6, further comprising providing a fourth portion of the sample fluid in the sensing channel after the third diffusion period and before providing the second portion of the sample fluid, and holding the fourth portion of the sample fluid in the sensing channel for a fourth diffusion period.

8. The method of claim 1, wherein each subsequent portion of the sample fluid directly replaces the prior portion after the prior portion's diffusion period.

9. The method of claim 1, wherein the sensing element comprises an optical sensing element or an electrochemical sensing element.

10. The method of claim 1, further comprising providing an air segment prior to providing the first portion of the sample fluid.

11. The method of claim 1, wherein the first diffusion period is in a range between 5 seconds and 20 seconds.

12. The method of claim 1, wherein a volume of the first portion is between 25% and 200% of a volume of the sensing channel.

13. The method of claim 1, wherein the sensing element includes three to fifteen electrodes.

14. The method of claim 13, wherein a first electrode of the sensing element detects a first constituent in the second portion of the sample fluid and a second electrode of the sensing element detects a second constituent in the second portion of the sample fluid different from the first constituent.

* * * * *